US012589079B2

(12) United States Patent
Xu

(10) Patent No.: US 12,589,079 B2
(45) Date of Patent: Mar. 31, 2026

(54) GENE DELIVERY SYSTEM AND APPLICATION THEREOF IN PREPARATION OF DRUGS FOR TREATMENT OF TUMORS

(71) Applicant: SHANGHAI CELL DIFF MEDICINE LTD., Shanghai (CN)

(72) Inventor: Hanjiang Xu, Shanghai (CN)

(73) Assignee: SHANGHAI CELL DIFF MEDICINE LTD., Shanghai (CN)

( * ) Notice: Subject to any disclaimer, the term of this patent is extended or adjusted under 35 U.S.C. 154(b) by 0 days.

(21) Appl. No.: 19/204,534

(22) Filed: May 10, 2025

(65) Prior Publication Data

US 2025/0352489 A1 Nov. 20, 2025

(30) Foreign Application Priority Data

May 16, 2024 (CN) .......................... 202410606194.3

(51) Int. Cl.
| | |
|---|---|
| *A61K 9/00* | (2006.01) |
| *A61K 9/51* | (2006.01) |
| *A61P 35/00* | (2006.01) |
| *C07K 14/47* | (2006.01) |
| *C12N 15/86* | (2006.01) |

(Continued)

(52) U.S. Cl.
CPC ............ *A61K 9/5146* (2013.01); *A61P 35/00* (2018.01); *C07K 14/47* (2013.01); *C12N 15/86* (2013.01); *C12N 15/88* (2013.01); *A61K 38/00* (2013.01); *C12N 2770/36143* (2013.01); *C12N 2830/50* (2013.01)

(58) Field of Classification Search
CPC .................................................. A61K 9/5146
See application file for complete search history.

(56) References Cited

U.S. PATENT DOCUMENTS

| | | | |
|---|---|---|---|
| 11,464,836 | B2 | 10/2022 | Horscroft et al. |
| 2011/0077206 | A1 | 3/2011 | Xie et al. |
| 2019/0343933 | A1 | 11/2019 | Horscroft et al. |

FOREIGN PATENT DOCUMENTS

| | | |
|---|---|---|
| CN | 101524529 A | 9/2009 |
| CN | 110582304 A | 12/2019 |

(Continued)

OTHER PUBLICATIONS

Machine Translation of CN101524529A (Year: 2025).*

(Continued)

*Primary Examiner* — Paul W Dickinson
(74) *Attorney, Agent, or Firm* — Central California IP Group, P.C.; Andrew D. Fortney

(57) ABSTRACT

A gene delivery system and applications thereof in the technical field of biological medicines that is particularly useful in the preparation of drugs for treatment of tumors are disclosed. The gene delivery system and applications relate to technology for inducing the differentiation of malignant tumor cells into mature cells, in which regulating the expression of HNF4 alpha protein in the malignant tumor cells using messenger ribonucleic acid, the malignant phenotype of the malignant solid tumor cells is inhibited, and the effective treatment of the malignant solid tumors is achieved. The gene delivery system and applications are therefore applicable to a method of preparing a drug for treating malignant solid tumors and to a method of treating a patient having a malignant solid tumor.

13 Claims, 22 Drawing Sheets

Specification includes a Sequence Listing.

(51) Int. Cl.
   *C12N 15/88* (2006.01)
   *A61K 38/00* (2006.01)

(56) References Cited

FOREIGN PATENT DOCUMENTS

| WO | WO-2020243719 A1 * | 12/2020 | ........... C07K 14/005 |
| WO | 2023/006999 A2 | 2/2023 | |
| WO | 2023/133489 A1 | 7/2023 | |

OTHER PUBLICATIONS

Machine Translation of CN110582304A (Year: 2025).*

Notice of Grant of Invention Patent, CN Pat. Appl. No. 202410606194. 3; Jul. 16, 2024; State Intellectual Property Office, Beijing, China.

Office Action, CN Pat. Appl. No. 202410606194.3; Jun. 24, 2024; State Intellectual Property Office, Beijing, China.

Hyeshik Chang et al.; "TAIL-seq: Genome-wide Determination of Poly(A) Tail Length and 30 End Modifications"; Molecular Cell 53, 1044-1052, Mar. 20, 2014; dx.doi.org/10.1016/j.molcel.2014.02. 007; Elsevier Inc.

Xuexiang Han et al.; "An ionizable lipid toolbox for RNA delivery"; Nature Communications (2021) 12:7233; doi.org/10.1038/s41467-021-27493-0; Springer Nature, New York, New York.

Product Information, SM-102; Cayman Chemical, Ann Arbor, MI.

Pengfei Ding et al., "Sequestering the 5'-Cap for viral RNA packaging"; Bioessays, Sep. 13, 2022; 44(11):e2200104, doi: 10.1002/bies.202200104.

Aysegül Yildiz et al.; "Trans-Amplifying RNA: A Journey from Alphavirus Research to Future Vaccines"; Viruses 2024, 16, 503. https://doi.org/10.3390/v16040503; MDPI, Basel, Switzerland.

Rebecca Bevans; "An Introduction to t Tests; Definitions, Formula and Examples"; Jan. 31, 2020; scribbr.com/statistics/t-test/.

Kenneth Lundstrom; "Nanoparticle-based delivery of self-amplifying RNA"; Gene Therapy (2020) 27:183-185; doi.org/10. 1038/s41434-020-0132-1; Springer Nature, New York, New York.

* cited by examiner

HCT116

HCT 116

13 weeks before treatment    Baseline    10 weeks after treatment    23 weeks after treatment Baseline    4 weeks after treatment    8 weeks after treatment    18 weeks after treatment 16 weeks after treatment    9 weeks after treatment    4 weeks after treatment    Baseline

SEQUENCE LISTING

```
Sequence total quantity: 3
SEQ ID NO: 1           moltype = DNA  length = 1425
FEATURE                Location/Qualifiers
source                 1..1425
                       mol_type = other DNA
                       organism = synthetic construct
SEQUENCE: 1
atgcgactct ccaaaaccct cgtcgacatg gacatggccg actacagtgc tgcactggac  60
ccagcctaca ccaccctgga atttgagaat gtgcaggtgt tgacgatggg caatgacacg  120
tccccatcag aaggcaccaa cctcaacgcg cccaacagcc tgggtgtcag cgccctgtgt  180
gccatctgcg gggaccgggc cacgggcaaa cactacggtg cctcgagctg tgacggctgc  240
aagggcttct tccggaggag cgtgcggaag aaccacatgt actcctgcag atttagccgg  300
cagtgcgtgg tggacaaaga caagaggaac cagtgccgct actgcaggct caagaaatgc  360
ttccgggctg gcatgaagaa ggaagccgtc cagaatgagc gggaccggat cagcactcga  420
aggtcaagct atgaggacag cagcctgccc tccatcaatg cgctcctgca ggcggaggtc  480
ctgtcccgac agatcacctc ccccgtctcc gggatcaacg gcgacattcg ggcgaagaag  540
attgccagca tcgcagatgt gtgtgagtcc atgaaggagc agctgctggt tctcgttgag  600
tgggccaagt acatcccagc tttctgcgag ctccccctgg acgaccaggt ggccctgctc  660
agagcccatg ctggcgagca cctgctgctc ggagccacca agagatccat ggtgttcaag  720
gacgtgctgc tcctaggcaa tgactacatt gtccctcggc actgcccgga gctggcggag  780
atgagccggg tgtccatacg catccttgac gagctggtgc tgcccttcca ggagctgcag  840
atcgatgaca atgagtatgc ctacctcaaa gccatcatct tctttgaccc agatgccaag  900
gggctgagcg atccagggaa gatcaagcgg ctgcgttccc aggtgcaggt gagcttggag  960
gactacatca acgaccgcca gtatgactcg cgtggccgct ttggagagct gctgctgctg  1020
ctgcccacct tgcagagcat cacctggcag atgatcgagc agatccagtt catcaagctc  1080
ttcggcatgg ccaagattga caacctgttg caggagatgc tgctgggagg gtcccccagc  1140
gatgcacccc atgcccacca ccccctgcac cctcacctga tgcaggaaca tatgggaacc  1200
aacgtcatcg ttgccaacac aatgcccact cacctcagca acggacagat gtgtgagtgg  1260
ccccgaccca ggggacaggc agccacccct gagaccccac agccctcacc gccaggtggc  1320
tcagggtctg agccctataa gctcctgccg ggagccgtcg ccacaatcgt caagcccctc  1380
tctgccatcc cccagccgac catcaccaag caggaagtta tctag              1425

SEQ ID NO: 2           moltype = DNA  length = 7695
FEATURE                Location/Qualifiers
source                 1..7695
                       mol_type = other DNA
                       organism = synthetic construct
SEQUENCE: 2
ataggcggcg catgagagaa gcccagacca attacctacc caaaatggag aaagttcacg  60
ttgacatcga ggaagacagc ccattcctca gagctttgca gcggagcttc ccgcagtttg  120
```

-continued

```
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatgggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatgagg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgaga   2160
cacgaccagc cgctccttac caagtaccaa ccatagggga gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttccagg ggtgggtgaa gcagttgcaa atagattaca   2760
aaggcaacga ataatgacg gcagctgcct ctcaagggct gacccgtaaa ggtgctgtatg   2820
ccgttcggta caaggtgaat gaaaatcctc tgtacgcacc cacctcagaa catgtgaacg   2880
tcctactgac ccgcacggag gaccgcatcg tgtggaaaac agccggc gaccatga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgg   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg ccagcgaaa   3840
gcatcattgg tgctatagcg cggcagttca gtttttcccg ggtatgcaaa ccgaaatcct   3900
cacttgaaga gacggaagtt ctgtttgtat tcattgggta gatcgcaag gcccgtaccg   3960
acaatcctta caagctttca tcaaccttga ccaacattta tacaggttcc agactccacg   4020
aagccgatg tgcaccctca tatcatgtgg tgcgaggggga tattgccacg gccaccgaag   4080
gagtgattat aaatgctgct aacagcaaag acaacctgg cggaggggtg tgcggagcgc   4140
tgtataagaa attcccggaa agcttcgatt tacagcgat cgaagtagga aaagcgcgac   4200
tggtcaaagg tgcagctaaa catatcattc atgccgtagg accaaactc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgcccgtc gaagagtcgg   4800
aagcctccac accacctagc acgctgcctt gcttgtgcat ccatgccatg actccagaaa   4860
```

-continued

```
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc    5520
caggcgtgaa tagggtgatc actagagagg agctcgaggc gcttacccg tcacgcactc     5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacag agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttgcga agacacataa tttgaatatg ttgcaggaca     6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtcgaccggc acagcgtgcc    7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggccggccg catacagcag caattggcaa gctgcttaca tagaactcgc ggcgattggc   7560
atgccgcctt aaaattttta ttttattttt cttttctttt ccgaatcgga ttttgttttt   7620
aatatttcaa aaaaaaaaaa aaaaaaaaaa aaaaaaaaaa aaaaaaaaaa aaaaaaaaaa   7680
aaaaaaaaaa aaaaa                                                     7695

SEQ ID NO: 3          moltype = DNA   length = 9120
FEATURE               Location/Qualifiers
source                1..9120
                      mol_type = other DNA
                      organism = synthetic construct
SEQUENCE: 3
ataggcggcg catgagagaa gcccagacca attacctacc caaaatggag aaagttcacg   60
ttgacatcga ggaagacagc ccattcctca gagctttgca gcggagcttc ccgcagtttg   120
aggtagaagc caagcaggtc actgataatg accatgctaa tgccagagcg ttttcgcatc    180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactca gctgaagaaa aactgtaagg   360
aaataactga taaggaattg gacaagaaaa tgaaggagct cgccgccgtc atgagcgacc   420
ctgacctgga aactgagact atgtgcctcc acgacgacga gtcgtgtcgc tacgaagggc   480
aagtcgctgt ttaccaggat gtatacgcgg ttgacgaca gcaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctgaca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
cgatgcaccg cgagggattc ttgtgctgca aagtgacaga cacattgaac ggggagaggg   1020
tctctttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
```

-continued

```
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtag    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc tttttgcttgt catgcaggta ctctcagagc gctcatagcc attataagac    2460
ctaaaaaggc agtgctctgc ggggatcca aacagtgcgg ttttttttaac atgatgtgcc    2520
tgaaagtgca tttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgtaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca gttttcccg ggtatgcaaa ccgaaatcct    3900
cacttgaaga dacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgaggggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaaag tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtga    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccacggttag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacacccc tggaggggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacaccgc    5520
caggcgtaga tagggtgatc actagagagg agctcgaggc gcttaccccg tcacgcactc    5580
ctagcaggtc ggtctcgaga accagcctgg tctccaaccc gccaggcgta aatagggtag    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgca    5880
acagaagcag ataccagtcc aggaaggtgg agaacatgaa agccataaca gctagacgta    5940
ttctgcaagg cctagggcat tatttgaagg cagaagaaa agtggagtgc taccgaaccc    6000
tgcatcctgt tcctttgtat tcatctagtg tgaaccgtgc ctttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
```

-continued

```
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct cttttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggccatgcg actctccaaa accctcgtcg acatggacat ggccgactac agtgctgcac 7560
tggacccagc ctacaccacc ctggaatttg agaatgtgca ggtgttgacg atgggcaatg 7620
acacgtcccc atcagaaggc accaacctca acgcgcccaa cagcctgggt gtcagcgccc 7680
tgtgtgccat ctgcggggac cgggccacgg gcaaacacta cggtgcctcg agctgtgacg 7740
gctgcaaggg cttcttccgg aggagcgtgc ggaagaacca catgtactcc tgcagattta 7800
gccggcagtg cgtggtggac aaagacaaga ggaaccagtg ccgctactgc aggctcaaga 7860
aatgcttccg ggctggcatg aagaaggaag ccgtccagaa tgagcgggac cggatcagca 7920
ctcgaaggtc aagctatgag gacagcagcc tgccctccat caatgcgctc ctgcaggcgg 7980
aggtcctgtc ccgacagatc acctcccccg tctccgggat caacggcgac attcgggcga 8040
agaagattgc cagcatcgca gatgtgtgtg agtccatgaa ggagcagctg ctggttctcg 8100
ttgagtgggc caagtacatc ccagctttct gcgagctccc cctggacgac caggtggccc 8160
tgctcagagc ccatgctggc gagcacctgc tgctcggagc caccaagaga tccatggtgt 8220
tcaaggacgt gctgctccta ggcaatgact acattgtccc tcggcactgc ccggagctgg 8280
cggagatgag ccgggtgtcc atacgcatcc ttgacgagct ggtgctgccc ttccaggagc 8340
tgcagatcga tgacaatgag tatgcctacc tcaaagccat catcttcttt gacccagatg 8400
ccaaggggct gagcgatcca gggaagatca agcggctgcg ttcccaggtg caggtgagct 8460
tggaggacta catcaacgac cgccagtatg actcgcgtgg ccgctttgga gagctgctgc 8520
tgctgctgcc caccttgcag agcatcacct ggcagatgat cgagcagatc cagttcatca 8580
agctcttcgg catggccaag attgacaacc tgttgcagga gatgctgctg ggagggtccc 8640
ccagcgatgc accccatgcc caccaccccc tgcaccctca cctgatgcag gaacatatgg 8700
gaaccaacgt catcgttgcc aacacaatgc ccactcacct cagcaacgga cagatgtgtg 8760
agtggccccg acccaggggga caggcagcca ccctgagac cccacagccc tcaccgccag 8820
gtggctcagg gtctgagccc tataagctcc tgccgggagc cgtcgccaca atcgtcaagc 8880
ccctctctgc catcccccag ccgaccatca ccaagcagga agttatctag ggccgcatac 8940
agcagcaatt ggcaagctgc ttacatagaa ctcgcggcga ttggcatgcc gccttaaaat 9000
ttttatttta tttttctttt cttttccgaa tcggattttg tttttaatat ttcaaaaaaa 9060
aaaaaaaaaa aaaaaaaaaa aaaaaaaaaa aaaaaaaaaa aaaaaaaaaa aaaaaaaaaa 9120
```

GENE DELIVERY SYSTEM AND APPLICATION THEREOF IN PREPARATION OF DRUGS FOR TREATMENT OF TUMORS

CROSS-REFERENCE TO RELATED APPLICATIONS

This application claims priority to Chinese Pat. Appl. No. 2024106061943, filed on May 16, 2024, the contents of each of which are incorporated by reference herein in their entireties.

REFERENCE TO AN ELECTRONIC SEQUENCE LISTING

The contents of the electronic sequence listing (SHCH-2402011US.xml; Size: 21,884 bytes; and Date of Creation: May 9, 2025) is incorporated herein by reference in its entirety.

TECHNICAL FIELD

The present disclosure belongs to the technical field of biological medicines, and particularly relates to a gene delivery system and application thereof in the preparation of drugs for treatment of tumors.

BACKGROUND ART

The treatment of malignant solid tumors is a current clinical difficulty, especially for malignant solid tumors that cannot be eradicated by surgery, and there is still a lack of effective treatment means in clinical practices. Although chemoradiotherapy, targeted therapy and immunotherapy have provided a variety of treatment therapies of tumors in recent years, chemotherapy resistance often occurs with the progression of tumors, and a large number of tumors lack effective targets for targeted drugs or are insensitive to immunotherapy, especially some gastrointestinal tumors such as liver cancer and pancreatic cancer, which lack effective drug treatment protocols, and the prognosis of patients is not optimistic.

Differentiation therapy for tumors is a strategy that promotes the differentiation of tumor cells into mature normal cells through various factors to restore the normal phenotype and function and to inhibit the proliferation of malignant tumor cells, which breaks the conventional thinking of tumor treatment. A classic example of differentiation therapy is the use of all-trans retinoic acid for differentiation treatment of acute promyelocytic leukemia, which has achieved good clinical efficacy and has been widely applied. However, treatment to induce differentiation of malignant solid tumors is still a difficult issue in current tumor treatment. Recent studies have found that transcription factors related to organ differentiation and development and function maintenance can induce the differentiation of related tumor cells into normal cells, and up-regulation of these differentiation-related transcription factors can inhibit the growth of tumor cells, but has no significant impact on the function of normal tissue cells, which opens up a new direction for differentiation therapy, especially for malignant solid tumors. Therefore, for tumors in different tissues, specific targeted regulation of proteins, molecules and genes closely related to tumor cell differentiation is a core issue of differentiation therapy. The use of genetic engineering technology to target and regulate the expression of important differentiation functional genes and thereby induce the phenotypic differentiation of tumor cells into mature cells has the potential to fundamentally reverse the process of malignant tumors.

The hepatocyte nuclear factor (HNF) family, which includes HNF1, HNF3, HNF4, HNF6, and CCAAT/enhancer binding protein (C/EBP), is a group of transcription factors predominantly expressed and regulated in the liver and plays a key role in liver development and function maintenance. Hepatocyte nuclear factor 4 alpha (HNF4 alpha) is a transcription factor belonging to the nuclear receptor family, which is expressed in liver, kidney, pancreas, intestine and other tissues, but is primarily expressed in mature hepatocytes. In mature hepatocytes, HNF4 alpha binds to about 12% of the gene promoters in cells, participates in the maintenance of important functions such as fat metabolism, albumin synthesis, drug detoxification, energy metabolism, and bile acid synthesis, and is also an important gene for maintaining the epithelial phenotype of hepatocytes. HNF4 alpha also regulates the development of kidney and gut tissues, and insulin production in pancreatic tissue. Previous studies have shown that the expression of HNF4 alpha decreases in various tumors of epithelial origin such as liver cancer (including hepatocellular cancer, intrahepatic cholangiocarcinoma), pancreatic cancer, intestinal cancer, and kidney cancer, and HNF4 alpha overexpression can inhibit tumor cell proliferation and metastasis and promote tumor cell apoptosis, suggesting that HNF4 alpha is a potential target for tumor treatment. HNF4 alpha has a total of 9 isoforms, and different isoforms depend on the transcriptional regulation of selective promoters P1 and P2 of HNF4 alpha. P1 promoter-regulated HNF4 alpha isoforms (HNF4 alpha 1-HNF4 alpha 6) are mainly expressed in the liver and kidney, P2 promoter-regulated HNF4 alpha isoforms (HNF4 alpha 7-HNF4 alpha 9) are mainly expressed in pancreatic and gastric tissues, and both P1 and P2 promoter-regulated HNF4 alpha isoforms are expressed in the intestinal tract. A patent entitled "HNF4 alpha-induced differentiation treatment for human malignant solid tumors" (Chinese patent number: ZL200810034200.3), previously owned by the inventor's team, used the overexpression of HNF4 alpha isoform 2 (HNF4 alpha 2) in hepatoma cells mediated by adenovirus vectors to clarify the therapeutic effect of HNF4 alpha on tumors.

In order to achieve effective tumor treatment, it should ensure long-term stable and efficient expression of HNF4 alpha in tumor cells. Due to the ability of rapid proliferation of tumors, tumor treatment requires repeated doses to ensure therapeutic effect. However, due to pre-existing immunity to adenovirus in the human population, and the ability of adenoviral vectors to induce an antiviral response in the human immune system, which further rejects the expression of genes of interest mediated by viral vectors in tumor cells, the dosing frequency for tumors with overexpression of HNF4 alpha using adenoviral vectors is therefore limited. On the other hand, previous studies have also shown that the adenoviral vectors have deficiencies in terms of safety and tissue targeting, and at the same time, the preparation costs are high, so the practical application potential of adenoviral vector-mediated HNF4 alpha overexpression is low for treatment of tumors.

mRNA technology is a revolutionary gene delivery technology developed in recent years. The technology synthesizes mRNA molecules with specific sequences by in vitro transcription, and uses lipid nanoparticles (LNPs) to encapsulate the mRNA and deliver it into human cells, which translate the mRNA into the protein of interest its own cellular translation system. This technology has good efficiency and safety compared with the existing viral vector-based delivery system. If combined with the screening and modification of nanolipid particles, the tissue specificity of the delivery system can be increased. At present, the known potential applications of mRNA technology mainly focus on the development of vaccines for infectious diseases, therapeutic tumor vaccines, protein replacement therapy for protein deficiency caused by genetic defects, and gene editing for the treatment of hereditary diseases or immune cell modification. However, due to the fact that mRNA can only mediate the transient high expression of genes of interest in cells, there are significant deficiencies in expression duration and expression efficiency, which may not meet the needs of long-term stable expression of the protein of interest in tumor cells with rapid proliferation ability.

Self-amplifying RNA (saRNA, or self-replicating RNA, srRNA) is a gene delivery vector technology based on the mRNA technology developed in recent years, which is a recombinant RNA with a viral structure. By engineering an alphavirus bicistronic genome, sequences encoding four nonstructural proteins (NSPs) from the virus can be retained, and the viral structural protein gene located the downstream of the viral subgenome promoter (SGP) is replaced with a heterologous gene of interest (GOI) encoding the protein of interest to construct an RNA vector capable of expressing genes of interest with the self-amplification ability in cells. At present, self-replicating RNA vectors are mainly engineered from Venezuelan equine encephalitis virus (VEEV), sindbis alphavirus (SIN) or Semliki Forest virus (SFV). Self-replicating RNA derived from Venezuelan equine encephalitis virus is the most commonly used. Self-replicating RNA enters the host cytoplasm and first translates four nonstructural proteins (NSP1, NSP2, NSP3, and NSP4), which are then polymerized through a complex and multi-step process to form RNA-dependent RNA polymerase complexes. The RNA polymerase complexes first synthesize complementary negative-strand RNA intermediates from positive-strand RNA, and then synthesize two different positive-strand RNAs from the latter as a template. The first positive-strand RNA is a copy of the original full-length genomic RNA; the second positive-strand RNA is a large number of subgenome RNAs encoding the gene(s) of interest. This mechanism enables self-replicating RNA to achieve high levels of long-lasting protein-of-interest expression at low doses of the self-replicating RNA. Self-replicating RNA retains the self-amplification ability of the viral genome, but lacks the ability to express the structural proteins of the virus, and therefore cannot produce intact, transmissible viruses. Its entry into cells depends on the delivery of lipid nanoparticles, which confer good safety and potential tumor targeting ability.

At present, self-replicating RNA is considered to be useful in the preparation of RNA vaccines and to mediate the expression of tumor killer cytokines in tumor cells in the treatment of tumors. For example, the Chinese patent application CN117280029A discloses a nucleic acid vector and method of use, which modulate the tumor microenvironment through the relative expression of activated tumor-infiltrating lymphocytes and/or immunogenic cell characteristics in the tumor microenvironment to achieve cancer treatment. The Chinese patent application CN117279661A discloses a composition and method for inducing an immune response to ESR1, PI3K, HER2 and HER3, which aims to treat cancer by inducing an immune response. The Chinese patent application CN115968299A discloses a neoantigen expressed in multiple myeloma and an application thereof, which also use self-replicating RNA as a vector to prepare tumor vaccines. Tumor vaccines work by expressing tumor antigens in antigen-presenting cells (APCs) such as dendritic cells (DCs), and presenting them to T cells of an immune system, activating the T cells to attack tumor cells to control or remove tumors.

However, the use of self-replicating RNA to express transcription factors in tumor cells, especially those related to differentiation of tissues and organs, has not been reported in the treatment of tumors.

SUMMARY

One purpose of the present disclosure is to use self-replicating RNA to mediate the overexpression of HNF4 alpha in tumor cells to induce the differentiation of tumor cells into mature cells, inhibit tumor cell growth, and provide a novel method for tumor treatment.

Hepatocyte nuclear factor 4 (HNF4) alpha is expressed at a lower level in relevant tumor cells than in normal cells. The inventor has found that the distribution of self-replicating RNA in tumor cells does not decrease with the rapid proliferation of tumor cells based on its self-replication characteristics, and can continuously express protein for 20 to 30 days or more after entering tumor cells, so it is very suitable for mediating the expression of the genes of interest in tumor cells. At the same time, animal experiments have shown that self-replicating RNA encapsulated in lipid nanoparticles injected into the tail vein can mediate the specific expression of the genes of interest in tumor tissues, while the expression of the genes of interest is basically undetectable in other normal tissues, indicating that self-replicating RNA has good tumor targeting. Based on these findings, restoration and/or overexpression of HNF4 alpha in tumor tissues using self-replicating RNA vectors to induce the differentiation of tumor cells into normal cells and inhibit tumor cell growth is disclosed, so as to provide a method of treating tumors.

According to the present disclosure, HNF4 alpha is introduced into tumor cells by self-replicating RNA technology for overexpression, which is specifically and long-term expressed in tumor cells, and achieves the purpose of treating tumors by inducing the differentiation of related tumor cells into mature cells.

The self-replicating RNA may optimize the length of the polyA tail to maintain long-lasting, high expression of the genes of interest in vivo. The structure of the self-replicating RNA includes a 5'-cap, a non-coding or untranslated region (5' UTR), four non-structural genes (e.g., genes encoding non-structural proteins NSP1-4), a 26S subgenome promoter (SGP), one or more genes of interest (GOI, which include a gene encoding HNF4 alpha), a 3' non-coding or untranslated region (3' UTR), and a polyadenylated tail (e.g., polyadenine or polyA). In order to optimize the performance of the self-replicating RNA, previous studies have tried multiple strategies to engineer NSP1-4, by introducing mutations to improve the replication efficiency and immunogenicity of self-replicating RNA, and increase the intensity and duration of expression of different genes of interest in cells. We found that self-replicating RNA vectors with NSP1-4 mutations did not differ much in their efficiency in mediating HNF4 alpha expression in tumor cells. Previous studies have shown that the length and sequence of the polyadenylated (polyA) tail of the mRNA affect the stability of the mRNA and ribosomal translation, and changing the length of the polyA tail can affect the expression duration and level of encoded proteins by regulating the degradation rate and translation level of mRNA. However, it is not clear whether the polyA tail of self-replicating RNA affects the expression duration and level of the genes of interest in tumor cells. In order to obtain a self-replicating RNA vector that can mediate stable and efficient expression of HNF4 alpha in tumor cells, we optimized the poly A tail length of the self-replicating RNA, and found that self-replicating RNA with a polyA length between 35 and 100 nt mediates the stable and long-term overexpression of HNF4 alpha in tumor cells. The expression level and duration are better at 60-75 nt. A 67 nt polyA tail has the most stable and efficient expression.

According to the present disclosure, the effects of non-replicating HNF4 alpha-mRNA and HNF4 alpha-saRNA and adenovirus-mediated overexpression of HNF4 alpha in tumor cells were investigated. The results showed that both HNF4 alpha-saRNA and HNF4 alpha-mRNA could up-regulate HNF4 alpha in hepatoma cells, but the expression level of HNF4 alpha-mRNA was low, and the expression duration was short. However, the expression of HNF4 alpha-saRNA was 2 times or more as high as that of HNF4 alpha-mRNA, with a longer duration. The effect of HNF4 alpha-mRNA on up-regulating HNF4 alpha expression could only be maintained for 3 days, while HNF4 alpha-saRNA could maintain HNF4 alpha in hepatoma cells for at least 7 days, and up-regulating expression efficiency of HNF4 alpha by HNF4 alpha-saRNA was not lower than that of adenovirus (i.e., the adenovirus itself).

A first aspect of the present disclosure provides a gene delivery system, comprising a nucleic acid vector and a delivery vehicle. The nucleic acid vector is a self-replicating RNA carrying or encoding HNF4 alpha (e.g., a gene encoding an HNF4 alpha protein), and the gene delivery system delivers the HNF4 alpha (or the self-replicating RNA including the gene encoding the HNF4 alpha protein) into tumor cells, induces differentiation of the tumor cells into normal mature cells, inhibits proliferation of the tumor cells, and/or induces apoptosis of the tumor cells.

A preferred HNF4 alpha, GENBANK number: NM_000457.6, has the sequence shown in SEQ ID NO: 1.

The self-replicating RNA further include a 5'-cap, a 5' non-coding or untranslated region, a plurality of non-structural genes, a 26S subgenome promoter, a 3' non-coding or untranslated region, and a polyadenylated (e.g., polyadenine or polyA) tail.

The self-replicating RNA has or carries a 35-100 nt polyadenine tail.

Preferably, the self-replicating RNA has or carries a 60-75 nt polyadenine tail.

More preferably, the self-replicating RNA has or carries a 67 nt polyadenine tail.

In a preferred example of the present disclosure, a sequence of the self-replicating RNA is shown in SEQ ID NO:3. The sequence is optimized for the polyA tail of wild-type self-replicating RNA, and preferably, the saRNA has a 67 nt polyA tail. The saRNA with the 67 nt polyA tail can increase the half-life of the saRNA in vivo and promote the stability and translation of the saRNA.

A gene delivery system is provided in which the delivery vehicle comprises (or is selected from) a liposome, viral replicon particles, lipid-based nanoparticles, polymer nanoparticles, a physiological buffer, microspheres, an immune-stimulating complex, a conjugates of two or more bioactive ligands, or a combination thereof.

Preferably, the delivery vehicle comprises the lipid-based nanoparticles (LNPs), comprising (or wherein one or more lipids of the LNPs includes):

1,2-distearoyl-sn-glycero-3-phosphocholine (DSPC) or 1,2-dioleoyl-sn-glycero-3-phosphorylethanolamine (DOPE) in an amount of 5%-20% of the LNPs by moles;

cholesterol, in an amount ranging from 30% to 55% of the LNPs by moles;

dimyristoylglycerol-polyethylene glycol 2000 (DMG-PEG 2000) or other pegylated lipids (e.g., a fatty acid-glycerol ester containing one or more polyethylene glycol chains, which may have a molecular weight of 500-10,000 g/mol), in an amount ranging from 0.5% to 3% of the LNPs by moles; and one or more ionizable lipids (e.g., N,N-bis [6-(2-hexyldecanoyl)oxyhexyl]-4-hydroxy-butylamine [ALC-0315], 8-[(2-hydroxyethyl) [6-oxo-6-(undecyloxy) hexyl]amino]-octanoic acid, 1-octylnonyl ester [SM-102], (2-hydroxyethyl)ethylazanediylbis(hexane-6,1-diyl)bis(2-hexyldecanoate) [DHA-1], etc.), in an amount ranging from 30% to 60% of the LNPs by moles.

For example, the ionizable lipid(s) may be an N-acyloxy-alkyl N-hydroxyalkylamine, and may have a formula $NR^1R^2R^3$, where $R^1$ is an ω-hydroxy-$C_2$-$C_{10}$-alkyl or an ω-hydroxy-$C_4$-$C_{10}$-dialkylene ether group, and $R^2$ and $R^3$ are independently a $C_4$-$C_{10}$-alkylene group substituted with a straight-chain or branched $C_{10}$-$C_{20}$-alkanoyloxy group.

In one preferred example of the present disclosure, the sum of the molar percentages of the lipids is 100%; and the composition of the lipids is DSPC: cholesterol: DMG-PEG 2000: ionizable lipid(s) in a molar ratio of 9.4:42.5:1.8:46.3.

An N: P ratio (i.e., the ratio of nitrogen in the ionizable lipid to phosphate groups in the mRNA) in the LNPs may range from 5:1 to 10:1, and preferably, is 6:1.

The LNPs may have a particle size of about 40-300 nm.

According to a second aspect of the present disclosure, the gene delivery system may be used in a method of preparing a drug effective for the treatment of solid malignant tumors and a method of treating a solid malignant tumor. For example, in some embodiments, the method of treating a solid malignant tumor comprises administering an effective amount of the present gene delivery system to a patient in need thereof.

In further embodiments, the malignant solid tumor treated by the method may be malignant solid tumor derived from epithelial cells.

In other or further embodiments, the malignant solid tumor is liver cancer, pancreatic cancer, gastric cancer, intestinal cancer, renal cancer, or lung cancer.

The method of preparing the gene delivery system, which may be effective for the treatment of solid malignant tumors, comprises preparing a self-replicating RNA including a gene encoding an HNF4 alpha protein, preparing a delivery vehicle, and mixing the self-replicating RNA and the delivery vehicle to form the gene delivery system. The delivery vehicle comprises a liposome, viral replicon particles, lipid-based nanoparticles, polymer nanoparticles, a physiological buffer, microspheres, an immune-stimulating complex, a conjugates of two or more bioactive ligands, or a combination thereof. When the gene delivery system is administered to tumor cells, the gene delivery system delivers the self-replicating RNA into the tumor cells, induces differentiation of the tumor cells into normal mature cells, inhibits proliferation of the tumor cells, and/or induces apoptosis of the tumor cells. The self-replicating RNA may include a 5'-cap, a 5' non-coding or untranslated region (5' UTR), four genes encoding non-structural proteins, a 26S subgenome promoter (SGP), one or more genes of interest (GOI) including a gene encoding the HNF4 alpha protein, a 3' non-coding or untranslated region (3' UTR), and a 35-100 nt polyadenine tail. The delivery vehicle may comprise lipid-based nanoparticles comprising 1,2-distearoyl-sn-glycero-3-phosphocholine or 1,2-dioleoyl-sn-glycero-3-phosphorylethanolamine in an amount of ranging from 5% to 20% by moles, cholesterol in an amount of ranging from 30% to 55% by moles, a lipid containing a polyethylene glycol chain in an amount of ranging from 0.5% to 3% by moles, and one or more ionizable lipids, in an amount of ranging from 30% to 60% by moles.

A third aspect of the present disclosure provides a pharmaceutical composition including the gene delivery system.

The present disclosure has the following technical effects: A self-replicating RNA vector based on an mRNA technology platform is employed, combined with a lipid nanoparticle-encapsulated delivery vehicle and method to highly express the important differentiation-related gene HNF4 alpha in tumor cells, induce the transformation of tumor cells into normal cells, inhibit the malignant phenotype of the tumor/tumor cells, and achieve the purpose of treating the malignant tumor(s). This is a brand-new means of inducing differentiation to treat malignant tumors. According to the results of previous animal experiments and investigator-initiated clinical studies, it can be confirmed that this technical approach can effectively inhibit the growth of tumors in the body, which is a brand-new solution for malignant tumor treatment and is expected to create a new track for malignant tumor treatment. There are obvious differences between the present disclosure and application of the current mRNA technology in tumor vaccines. RNA tumor vaccines use RNA technology to express relevant tumor antigens in antigen-presenting cells to stimulate the body to produce immune responses to these antigens, thereby playing a role in controlling or removing the tumors. According to the present disclosure, the RNA technology is employed to mediate the expression of a transcription factor HNF4 alpha in malignant tumor cells, which exerts the effect of HNF4 alpha in promoting differentiation of the cells, and then inhibits the malignant phenotype of tumors. Although non-replicating mRNA also mediates the transient expression of genes of interest in the tumor cells, in order to induce the differentiation of malignant tumor cells into normal cells, HNF4 alpha needs to be expressed stably and efficiently in the malignant tumor cells. Therefore, for the first time, the present disclosure concerns a self-replicating RNA technology that is used to restore or overexpress HNF4 alpha (whose expression is downregulated during tumorigenesis), inhibit tumor cell growth, and achieve the effect of malignant tumor treatment. Therefore, the gene delivery system provided by the present disclosure can induce differentiation of malignant solid tumor cells into normal mature cells, inhibit the proliferation of malignant tumor cells, and induce tumor cell apoptosis. At the same time, according to the present disclosure, the self-replicating RNA vector is optimized to obtain a delivery system that can stably and efficiently express HNF4 alpha in malignant tumor cells.

In summary, according to the present disclosure, the self-replicating RNA is employed to express HNF4 alpha, which not only has a high expression level and high expression efficiency, but also has a longer duration. For example, preferably, HNF4 alpha-saRNA according to the present disclosure can maintain HNF4 alpha for 7 days or more in hepatoma cells, and the level and duration of expression is much higher than that of non-replicating HNF4 alpha-mRNA. Compared with viral vectors, the HNF4 alpha-saRNA has the advantages of good safety, strong tissue accessibility, reproducible administration and the like, and the therapeutic effect has been observed in tumor-bearing animals and in human patients.

BRIEF DESCRIPTION OF THE DRAWINGS

FIG. 36A: Liver cancer target lesion within 13 weeks prior to treatment (dotted box); FIG. 36B: Liver cancer target lesion at baseline was significantly enlarged compared with that of FIG. 36A; FIG. 36C: Liver cancer target lesion size remained stable 10 weeks after treatment; FIG. 36D Liver cancer target lesion size remained stable 23 weeks after treatment, with liquefactive necrosis in some areas (arrow).

FIG. 37A: Lung metastatic lesion of liver cancer at baseline (arrows); FIG. 37B: Lung metastatic lesion of liver cancer increased slightly from baseline at 4 weeks after treatment; FIG. 37C: Lung metastatic lesion of liver cancer 8 weeks after treatment was slightly smaller than in FIG. 37B; FIG. 37D: Lung metastatic lesion of liver cancer further shrank 18 weeks after treatment, and a diameter of the lesion was significantly smaller than the baseline level.

FIG. 38A: Liver cancer target lesion (dotted lines) at an arterial phase were significantly enhanced at baseline; FIG. 38B: Liver cancer target lesion increased from baseline 4 weeks after treatment, and enhancement at the arterial phase weakened compared with FIG. 38A; FIG. 38C: Liver cancer target lesion was further enlarged 9 weeks after treatment, and enhancement at the arterial phase was further weakened; FIG. 38D: Liver cancer target lesion continued to enlarge 16 weeks after treatment, enhancement at the arterial phase continued to weaken, and enhancement in most areas disappeared (arrow).

DETAILED DESCRIPTION OF EMBODIMENTS

Figures 1, 2:
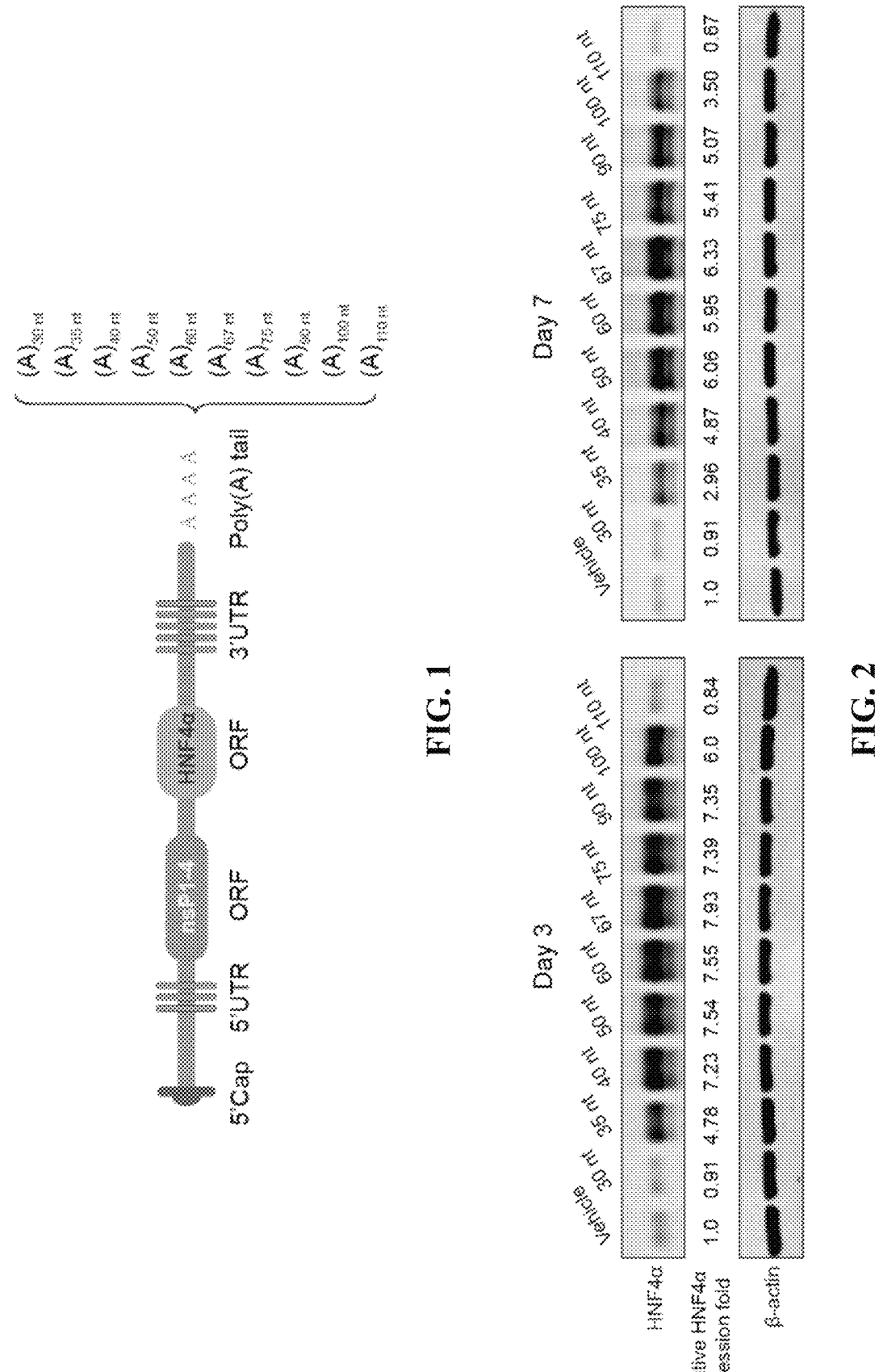
FIG. 1 is a structural schematic diagram illustrating HNF4 alpha-expressing self-replicating RNAs with polyA tails having different lengths. The gene of interest (GOI) is HNF4 alpha; the lengths of the polyA tails are 30 nt, 35 nt, 40 nt, 50 nt, 60 nt, 67 nt, 75 nt, 90 nt, 100 nt, and 110 nt.
FIG. 2 shows the effect of polyA length on overexpression of self-replicating RNA-mediated HNF4 alpha in hepatoma cells, as indicated by treating Huh-7 cells with HNF4 alpha-expressing self-replicating RNA lipid nanoparticles (HNF4 alpha-saRNA LNP) with different polyA tail lengths, respectively collecting cellular proteins 3 days and 7 days post-transfection, and detecting the expression level of HNF4 alpha protein after different treatments by western blot.

The specific implementations of the present disclosure will be described in detail below with reference to examples. The advantages and features of the present disclosure will become clearer with the description. However, these examples are merely exemplary, and are not construed as any limitation to the scope of the present disclosure. It should be understood by those skilled in the art that modifications or replacements can be made to the details and form of the technical solutions of the present disclosure without departing from the spirit and scope of the present disclosure, and these modifications and replacements all fall within the protection scope of the present disclosure.

Unless otherwise described, examples of the present disclosure will employ conventional techniques of molecular biology, cell biology and immunology, which are known to those skilled in the art. These techniques are fully described in the following literature: e.g., Experimental Guidelines for Molecular Cloning 4th Edition (2017); Experimental Guidelines for Refined Cell Biology (2007); Experimental Guidelines for Refined Immunology (2010). Alternatively, the instructions for use provided by the reagent or kit manufacturer may be followed.

Percentages and parts are calculated by weight unless otherwise noted. Unless otherwise defined, all professional and scientific terms used herein have the same meaning as those familiar to a person of well-trained skill in the art. In addition, any method and material which is similar with or equivalent to the mentioned content can be applied to the present disclosure. The preferred implementation methods and materials described herein only achieve a demonstration effect.

All data herein is analyzed and graphed using GraphPad Prism 8 software. All data error values are presented as mean±standard error (±SEM). Comparisons between two sets of data were performed using a two-tailed t-test, where $p < 0.05$ is considered statistically significant, * represents $p < 0.05$,  represents $p < 0.01$, * represents $p < 0.001$.

Example 1: Preparation of Self-Replicating RNA and LNP Encapsulation

1. Preparation of Linear mRNA and Self-Replicating RNA

Self-replicating RNA (saRNA) is based on an engineered alphavirus genome that contains genes encoding nonstructural proteins that enable RNA replication, while structural protein sequences are replaced by target gene sequences. saRNA includes a 5'-cap, a non-coding or untranslated region (5' UTR), four non-structural genes (NSP1-4), a 26S subgenome promoter, one or more genes of interest, a 3' non-coding or untranslated region (3' UTR), and a polyadenylated (polyA) tail. Linear RNA is designed from a eukaryotic mRNA structure and contains genes encoding protein of interest, as well as a requisite cap structure, a 5' UTR, a 3' UTR, and a poly(A) tail. Non-self-replicating RNA and self-replicating RNA were prepared in a consistent manner, starting with a linear template. In order to prepare the linear template for RNA transcription, plasmid DNA was restriction-digested with BspQI enzyme (New England Biolabs, R0712L), and purified and recovered using a PureLink® PCR purification kit (Invitrogen, K310002). T7 RNA polymerase (Promega, P1300), 1000 U/ml RNase inhibitor (New England Biolabs, M0314L), 2 U/ml inorganic pyrophosphatase (New England Biolabs, M2403L), 5 mM NTPs (New England Biolabs, N0466S), and cap analogs (3' OMe, Trinlink, N-7413) were prepared into a mixture for transcription. The mixture was mixed and incubated for 2 hours at 37° C. for in vitro transcription of the template. After the transcription reaction, DNase I (1 U/μg DNA) was added and incubated at 37° C. for 15 minutes to remove the DNA template, and then the transcribed RNA was purified and recovered using LiCl precipitation. 2. LNP-encapsulated RNA Lipid nanoparticles were prepared by rapid mixing of ethanolic and aqueous phases in a microfluidic device (INano™ L system, Micro & Nano). The aqueous phase was 50 mM citrate buffer (pH 6.0) containing purified saRNA. The ethanolic phase contained LP-1 (i.e., proprietary ionizable lipids), 1,2-distearoyl-sn-glycerophosphocholine (DSPC) (e.g., 850365P, commercially available from Avanti Polar Lipids, Inc., Alabaster, AL, USA), cholesterol (e.g., C8667, commercially available from Sigma-Aldrich, c/o Merck Co., Ltd., Chengdu, China), and 1,2-diacyl-sn-glycero-3-phosphoethanolamine-N-[methoxy (polyethylene glycol)-2000] (e.g., GM020, commercially available from NOF Europe GmbH, Frankfurt am Main, Germany). mRNA-LNPs were assembled in a molar ratio of 9.4:42.5:1.8:46.3 (DSPC:cholesterol: DMG-PEG 2000: LP-1), with N/P=6. LNPs formed from this formulation were tested for particle size, PDI, RNA concentration, and encapsulation rate.

Example 2: Optimization of polyA Tail Length of Self-Replicating RNA

LNP-encapsulated HNF4 alpha-expressing self-replicating RNAs with polyA tails of different lengths (HNF4 alpha-saRNA LNP) were prepared according to the method in Example 1 and as shown in FIG. 1. Hepatoma cells Huh7 were seeded into a 6-well plate at $3 \times 10^5$ cells/well and cultured overnight. HNF4 alpha-saRNA LNPs with different polyA lengths diluted in Opti-MEM were added separately, and after incubation for 6 hours, 1 mL of DMEM medium containing 20% FBS was added. Transfected cells were collected with RIPA lysate after 3 days or 7 days for the detection of intracellular protein level of HNF4 alpha by Western blot (FIG. 2). The results show that HNF4 alpha-saRNA with a polyA tail length of 35-100 nt mediate HNF4 alpha overexpression in Huh-7 cells. HNF4 alpha expression was higher in tumor cells transfected with self-replicating RNA with a polyA tail length of 40-90 nt. However, the self-replicating RNA with polyA tail length of 60-75 nt showed better HNF4 alpha expression level and expression duration, and the self-replicating RNA with polyA tail at 67 nt mediates the most efficient expression. The self-replicating RNA sequence with the best experimental effect on the optimization of the polyA tail length is shown in SEQ ID NO:2, and the sequence of HNF4 alpha-saRNA is shown in SEQ ID NO:3 (this sequence was adopted in all subsequent examples).

Figures 3, 4:
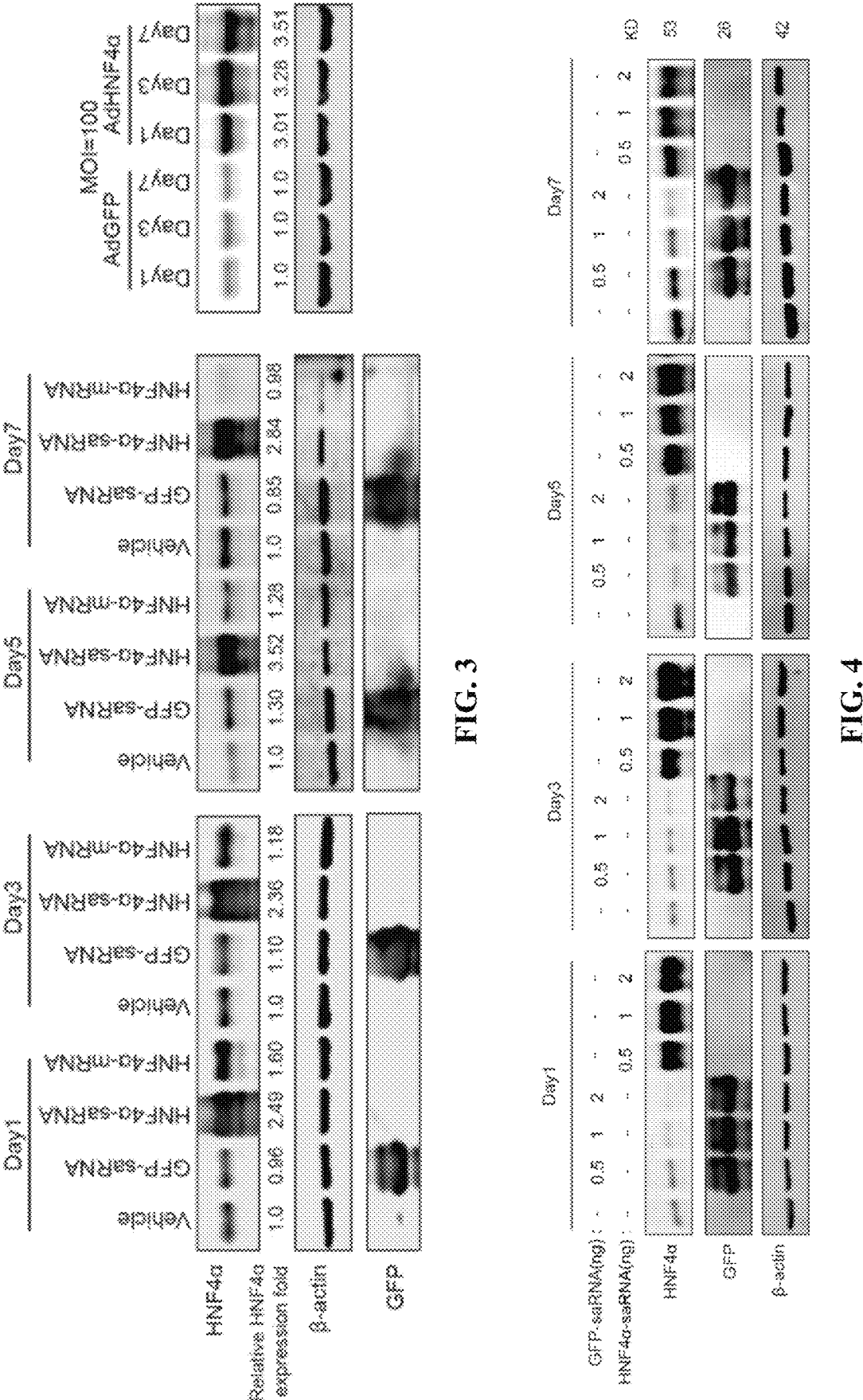
FIG. 3 shows western blots of proteins collected after Huh7 cells were treated with HNF4 alpha-saRNA and HNF4 alpha-mRNA lipid nanoparticles at 2 ng/200 cells for 1, 3, 5 and 7 days, respectively. In parallel, proteins were collected after infection of Huh7 cells by adenovirus Ad-HNF4 alpha and control virus Ad-GFP for 1, 3 and 7 days, respectively. The expression level of HNF4 alpha protein after the different treatments was detected by western blot. Image J software counted the relative expression of HNF4 alpha protein at each time point.
FIG. 4 shows the protein expression level of HNF4 alpha by western blot analysis after Huh-7 cells were treated with different concentrations of HNF4 alpha-saRNA and control GFP-saRNA lipid nanoparticles for 1, 3, 5 and 7 days. GFP-saRNA is a self-replicating RNA control.

Example 3: Comparison of Non-Replicating HNF4 Alpha-mRNA, HNF4 Alpha-saRNA, and Adenovirus AdHNF4 Alpha to Mediate HNF4 Alpha Overexpression in Tumor Cells Hepatoma cells Huh7 were seeded at $3 \times 10^5$ cells/well into a 6-well plate and cultured overnight. After washing with 1 ml of PBS, 1 ml of Opti-MEM diluted HNF4 alpha-saRNA LNP, control GFP-saRNA LNP, and non-replicating HNF4 alpha-mRNA LNP (final concentration of 2 ng RNA/200 cells) were added. After incubation for 6 hours, 1 mL of DMEM medium containing 20% FBS was added. Transfected cells were collected with RIPA lysate after 1, 3, 5, or 7 days for the detection of intracellular protein levels of HNF4 alpha by Western blot (FIG. 3). The effect of adenovirus-mediated HNF4 alpha overexpression was compared with that adenovirus-mediated HNF4 alpha overexpression in Huh7 cells treated with HNF4 alpha-expressing adenovirus AdHNF4 alpha and its control virus AdGFP (FIG. 3). The results show that both HNF4 alpha-saRNA and HNF4 alpha-mRNA up-regulate HNF4 alpha in hepatoma cells, but the expression level of HNF4 alpha-mRNA was relatively low with a relatively short expression duration. However, HNF4 alpha-saRNA had a high expression level and a long duration, and its expression efficiency was not lower than that of adenovirus.

Example 4: HNF4 Alpha-saRNA Treatment of Liver Cancer by Inducing Differentiation of Hepatoma Cells into Hepatocytes 1. Different concentrations of HNF4 alpha-saRNA LNPs upregulated HNF4 alpha expression in liver cancer Huh-7 cells Hepatoma cells Huh7 were seeded at $3 \times 10^5$ cells/well into a 6-well plate and cultured overnight. After washing with 1 ml PBS, HNF4 alpha-saRNA LNP, control GFP-saRNA LNP were added separately with serial dilution in Opti-MEM (to a final concentration of 0.5, 1 or 2 ng RNA/200 cells). After incubation for 6 hours, 1 mL of DMEM medium containing 20% FBS was added. Transfected cells were collected with RIPA lysate after 1, 3, 5, or 7 days for the detection of intracellular protein levels of HNF4 alpha by Western blot (FIG. 4). The results show that HNF4 alpha-saRNA LNP upregulate the expression of HNF4 alpha, whereas control GFP-saRNA LNP did not affect HNF4 alpha expression in hepatoma cells.

2. HNF4 alpha-saRNA LNP inhibited the growth of hepatoma cells

Figure 5:
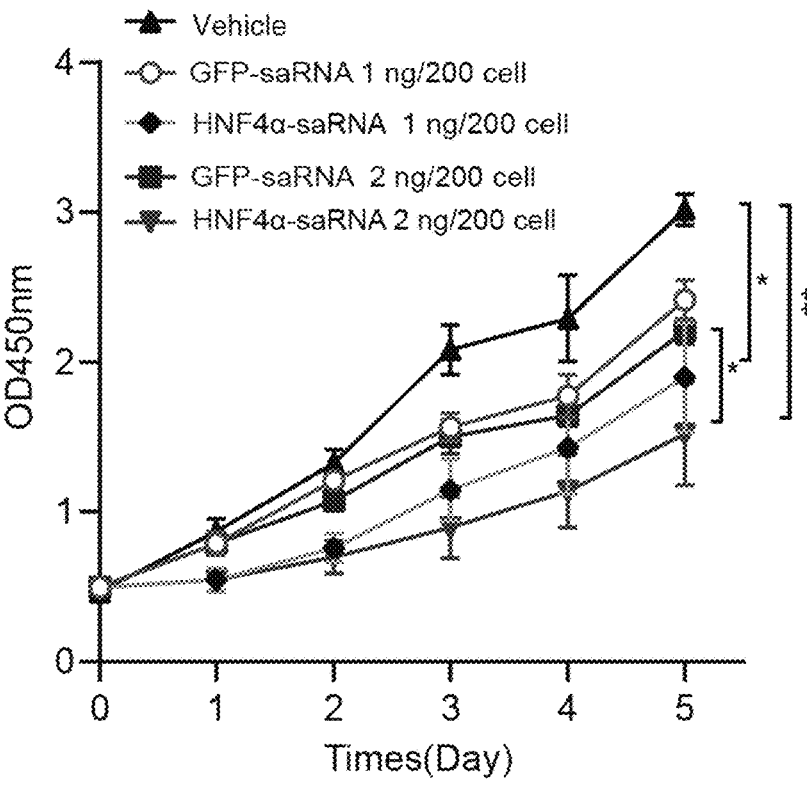
FIG. 5 is a graph that shows cell proliferation changes detected using CCK8 after Huh-7 cells were treated with different concentrations of HNF4 alpha-saRNA and GFP-saRNA lipid nanoparticles.

Hepatoma cells Huh7 were used to validate the inhibition of malignant phenotype of tumor cell proliferation and clonality by the gene delivery system. Huh7 cells were seeded separately in a 96-well plate at a density of $3 \times 10^3$ cells/well, and after overnight culture, a medium supernatant was pipetted and the cells were washed with 100 μl PBS. Different concentrations of HNF4 alpha-saRNA LNP and control GFP-saRNA LNP diluted in Opti-MEM were added to the cells. After 6 hours, an equal volume of 20% FBS was added to the culture fluid of the corresponding cells to produce a 10% FBS concentration in the culture fluid. Cell proliferation was measured daily using a cell counting kit-8 (CCK-8, commercially available from Dojindo Laboratories, c/o Dongren Chemical Technology (Shanghai) Co., Ltd., Shanghai, China) to clarify the effect of RNA on tumor cell proliferation ability. The results show that HNF4 alpha-saRNA LNP significantly inhibit the proliferation of hepatoma cells compared with control cells (FIG. 5).

Figure 6:
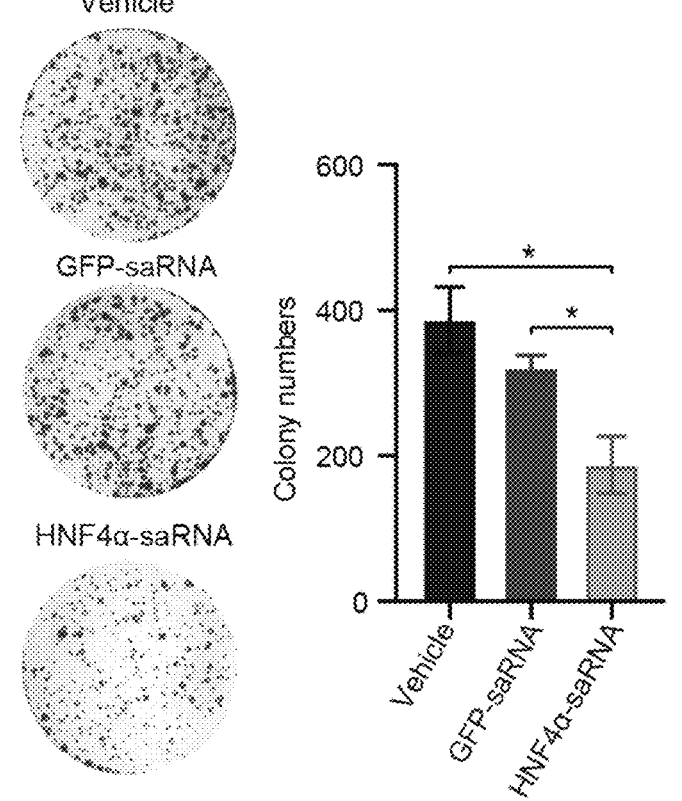
FIG. 6 shows effects of HNF4 alpha-saRNA and GFP-saRNA lipid nanoparticle treatment on the clonality of Huh7 hepatoma cells.

Next, an experiment was performed on the effect of the gene delivery system on the clonality of tumor cells. Hepatoma cells Huh7 were seeded in 96-well plates at a density of $3 \times 10^3$ cells/well, incubated overnight, and transfected with HNF4 alpha-saRNA LNP and control GFP-saRNA LNP (2 ng/200 cell). After 24 hours, the trypsinized cells were transferred to a 60 mm culture dish and cultured. The culture fluid was changed every 3 days, and the clonality of tumor cells was observed microscopically. After cloning, the cloned tumor cells were washed with PBS twice, stained with crystal violet for 20 minutes, washed with PBS, dried and photographed, and the number of clones was counted by image J to clarify the effect of RNA on the clonality of tumor cells. As shown in FIG. 6, HNF4 alpha-saRNA significantly inhibited the clonality of hepatoma cells.

Figure 7:
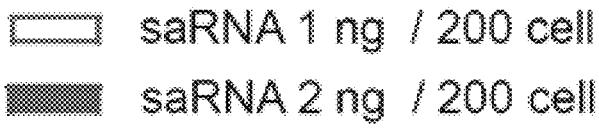
FIG. 7 is a bar graph that shows the detection of liver function-related genes by RT-PCR after Huh7 cells were treated with different concentrations of HNF4 alpha-saRNA and GFP-saRNA lipid nanoparticles for 3 days.
Figure 7:
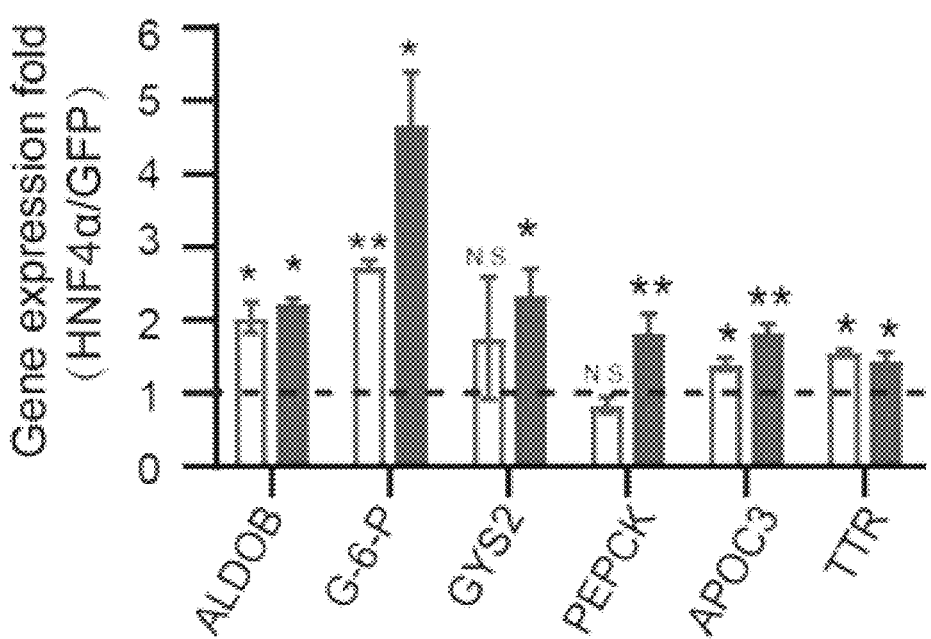
Figure 8:
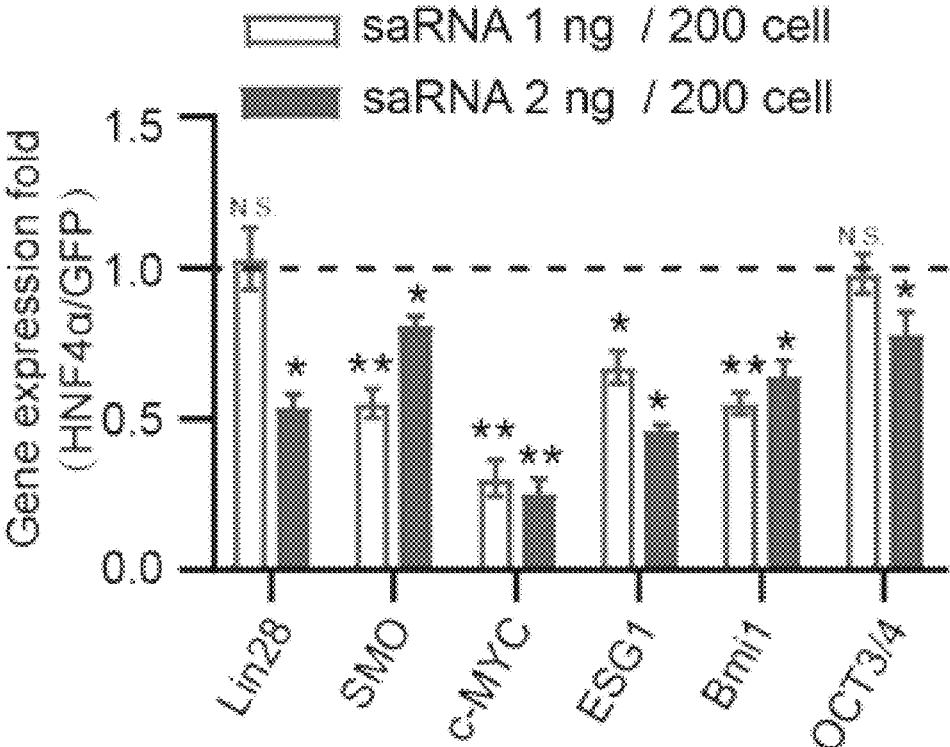
FIG. 8 shows the expression levels of stemness-related genes in tumor cells after Huh7 cells were treated with different concentrations of HNF4 alpha-saRNA and GFP-saRNA lipid nanoparticles for 3 days.

3. HNF4 alpha-saRNA LNP induced differentiation of hepatoma cells into mature hepatocytes ①HNF4 alpha-saRNA restored hepatic function gene expression in hepatoma cells Liver cancer cells Huh-7 were seeded into a 6-well plate at $3 \times 10^5$ cells/well and were cultured overnight. Cells were washed with PBS and different concentrations of HNF4 alpha-saRNA LNP and GFP-saRNA LNP diluted in Opti-MEM were added. After incubation for 6 hours, 1 mL of DMEM medium containing 20% FBS was added. RNA was extracted from cells collected 1, 3, or 7 days after cell transfection, and the expression of liver function-related genes regulated by HNF4 alpha and tumor stemness-related genes was detected by real-time fluorescence quantitative PCR (FIG. 7 and FIG. 8). The results show that HNF4 alpha-saRNA upregulates the expression of liver function-related genes and downregulates the expression of tumor stemness-related genes.

②HNF4 alpha-saRNA promoted glycogen storage and low-density lipoprotein uptake in hepatoma cells Glycogen storage and low-density lipoprotein uptake are important functions of normal hepatocytes, and these functions were further examined to determine whether hepatoma cells differentiate into mature hepatocytes.

Figure 9:
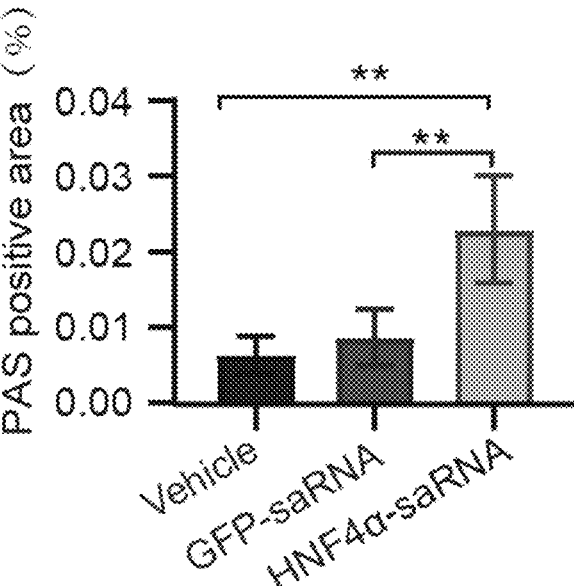
FIG. 9 shows a PAS positive area in Huh7 cells counted by image J software after Huh-7 cells were treated with HNF4 alpha-saRNA and GFP-saRNA lipid nanoparticles for 3 days, and glycogen storage in Huh-7 cells was detected by periodic acid-Schiff (PAS) staining.

Hepatoma cells Huh7 were seeded at $3 \times 10^4$ cells/well into a 24-well plate, and 1 ng/200 cells HNF4 alpha-saRNA LNP and corresponding control were added. Cellular glycogen storage capacity was verified using a periodic acid-Schiff (PAS) reaction kit (commercially available from Beyotime Biotechnology, Shanghai, China) 3 days after LNP delivery. The cells were fixed with 70% ethanol for 10 minutes, after which a periodic acid solution was taken and equilibrated to room temperature. 100 μl of the periodic acid solution was added dropwise to each sample, and after reaction in a wet box protected from light for 10 minutes, the periodic acid solution was removed. The samples were soaked in PBS and washed on a shaker for 5 minutes. 100 μl of Schiff reagent was added dropwise to each sample, placed in a wet box, and the wet box was placed in an oven at 37° C. for 1 hour in the dark. The staining solution was removed, and the cells were soaked in PBS and washed on a shaker for 5 minutes. Finally, 100 μl of hematoxylin staining solution was added dropwise in each sample for staining for 30 seconds. The staining solution was removed and the cells were washed with PBS twice to wash away the floating color. Photographs were taken under the microscope and statistics were performed (e.g., the PAS positive areas were determined) on the stained cells (FIG. 9). The results show that HNF4 alpha-saRNA promotes glycogen storage capacity of hepatoma cells.

Figure 10:
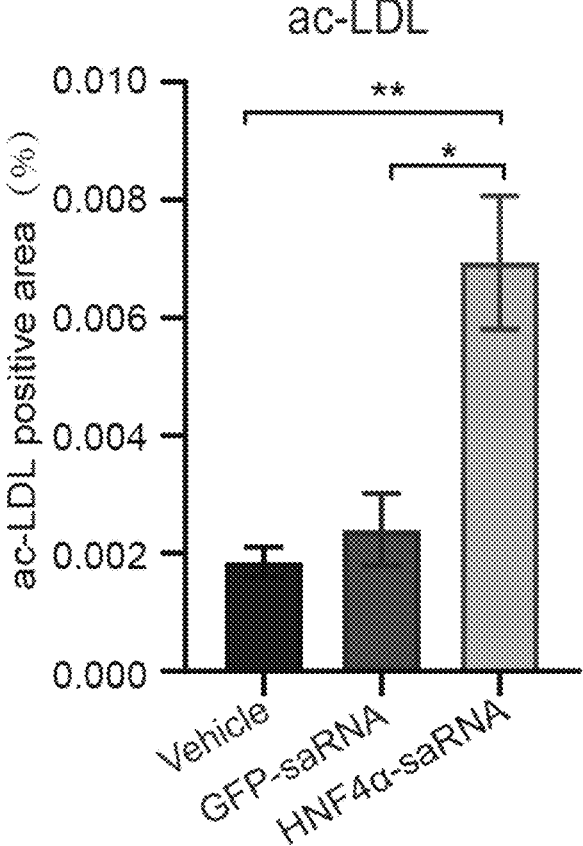
FIG. 10 shows uptake capacity of Huh7 cells for acetylated low-density lipoprotein (ac-LDL) using Dil-ac-LDL fluorescent substrates after Huh7 cells were treated with HNF4 alpha-saRNA and GFP-saRNA lipid nanoparticles for 3 days, and quantification of an ac-LDL positive area in Huh7 cells was counted by image J software.

Hepatoma cells Huh7 were seeded at $3 \times 10^4$ cells/well into a 24-well plate, and 1 ng/200 cells HNF4 alpha-saRNA LNP and corresponding controls (saline solution or GFP-saRNA LNP) were added. 3 days after LNP delivery, the cell culture medium was pipetted, the cells were washed with PBS, and then 200 μl per well of Dil ac-LDL (Invitrogen) diluted 1:100 with DMEM was added. DMEM containing Dil ac-LDL was removed after 3 h, then the cells were washed with PBS and fixed for 15 min with 4% paraformaldehyde. After staining with DAPI, the cells were mounted and photographed using a confocal fluorescence microscope, and statistics were performed (e.g., the ac-LDL positive areas were determined) on the fluorescence signals (FIG. 10). The results show that HNF4 alpha-saRNA promotes low-density lipoprotein uptake in hepatoma cells.

③ HNF4 alpha-saRNA promoted senescence of hepatoma cells

Figure 11:
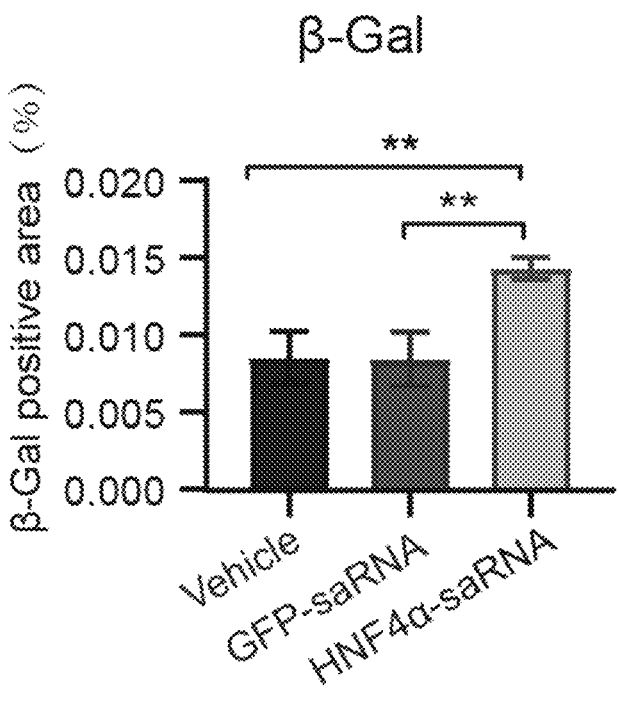
FIG. 11 shows quantification of a beta-galactosidase positive area in Huh7 cells counted by image J software after Huh7 cells were treated with HNF4 alpha-saRNA and GFP-saRNA lipid nanoparticles for 3 days and an amount of beta-galactosidase associated with senescence was detected in Huh7 cells.

Hepatoma cells Huh7 were seeded at $3 \times 10^4$ cells/well into a 24-well plate, and 1 ng/200 cells HNF4 alpha-saRNA LNP and corresponding controls (a saline vehicle alone or GFP-saRNA LNP) were added. Senescence of HCC cells was assessed 3 days after LNP delivery using a senescence beta-galactosidase staining kit (commercially available from Beyotime Biotechnology, Shanghai, China). Cells were fixed with 4% formaldehyde for 15 minutes and then incubated overnight at 37° C. with a fresh aging-related beta-galactosidase staining solution. Senescent cells were observed and captured under a microscope. The number of senescent cells was calculated using image analysis software (Image-Pro Plus 6.0, commercially available from Media Cybernetics, Buckinghamshire, UK) (FIG. 11). The results show that senescent hepatoma cells increases significantly after HNF4 alpha-saRNA treatment.

④ HNF4 alpha-saRNA induced apoptosis of hepatoma cells

Figures 12, 13:
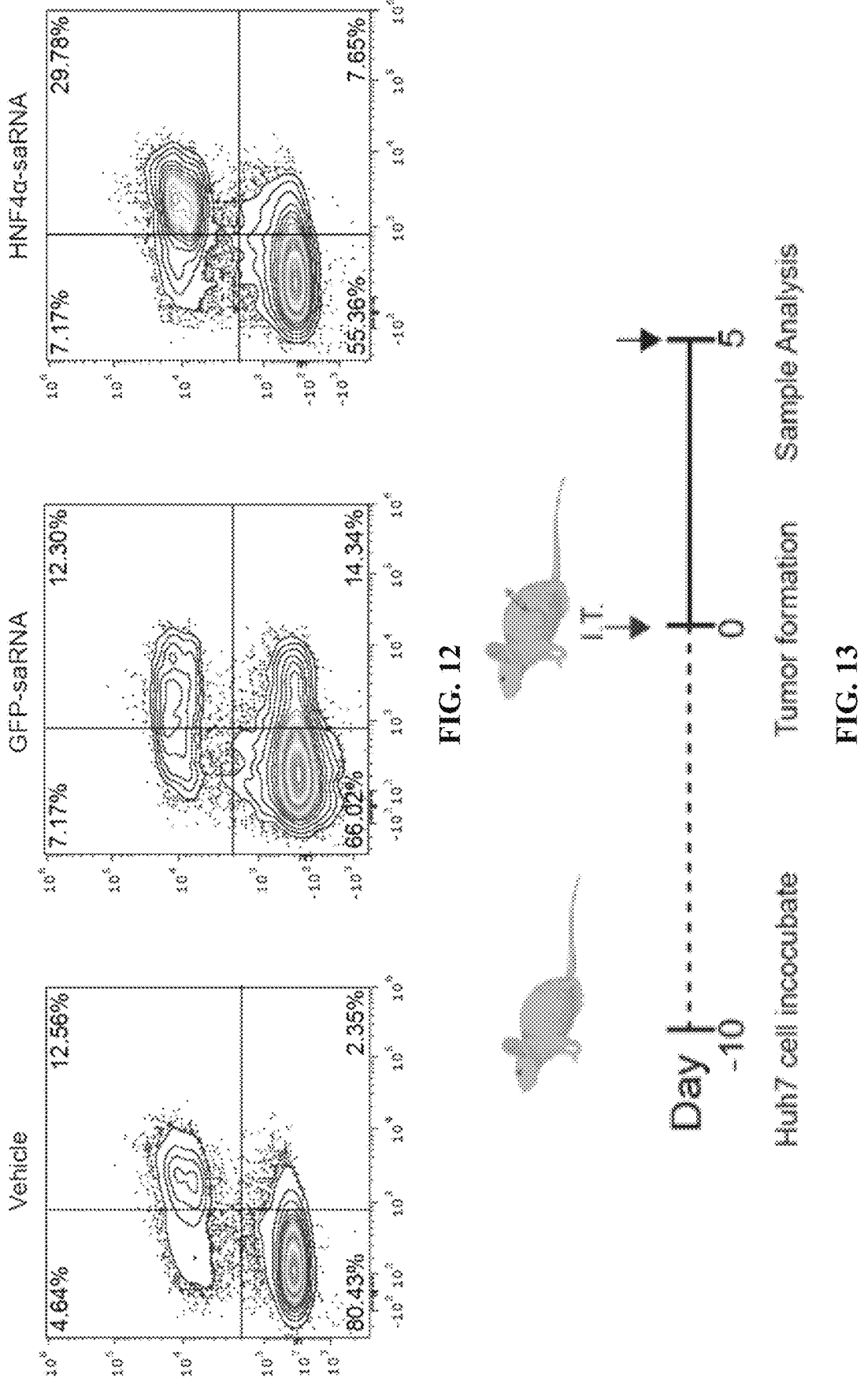
FIG. 12 shows apoptosis of Huh7 cells treated with HNF4 alpha-saRNA and GFP-saRNA lipid nanoparticles for 3 days by Annexin V/PI staining.
FIG. 13 is an experimental flow diagram illustrating intratumoral injection of HNF4 alpha-saRNA and HNF4 alpha-mRNA lipid nanoparticles in the treatment of subcutaneous xenografts of Huh7 cells in test animals.

Hepatoma cells Huh7 were seeded at $3 \times 10^5$ cells/well into a 24-well plate, and 1 ng/200 cells HNF4 alpha-saRNA LNP and corresponding controls (a saline vehicle alone or GFP-saRNA LNP) were added. The detection of apoptotic cells was performed 3 days after LNP delivery using an APC Annexin V/PI Apoptosis Kit (commercially available from Biolegend (Beijing) Ltd., Beijing, China) according to instructions for use provided by the manufacturer. Cells were 0.25% trypsinized and washed twice with PBS. Cells were then transferred to tubes and suspended in 100 µl of binding buffer. 400 µl of binding buffer containing 5 µl of APC Annexin V and 5 µl of propiodide were added to each tube for incubating at 25° C. for 15 minutes in the dark. Afterwards, cells were analyzed using a flow cytometer (Attune NxT, Invitrogen). Flow cytometry data were analyzed using FlowJo V10 software (FIG. 12). The results (FIG. 12) showed a significant increase in apoptosis of hepatoma cells treated with HNF4 alpha-saRNA relative to both the vehicle and GFP-saRNA LNP.

These findings suggest that HNF4 alpha-saRNA promotes the transformation and differentiation of hepatoma cells into mature hepatocytes, restores hepatocyte function, and further induces senescence and apoptosis of hepatoma cells.

Figure 14:
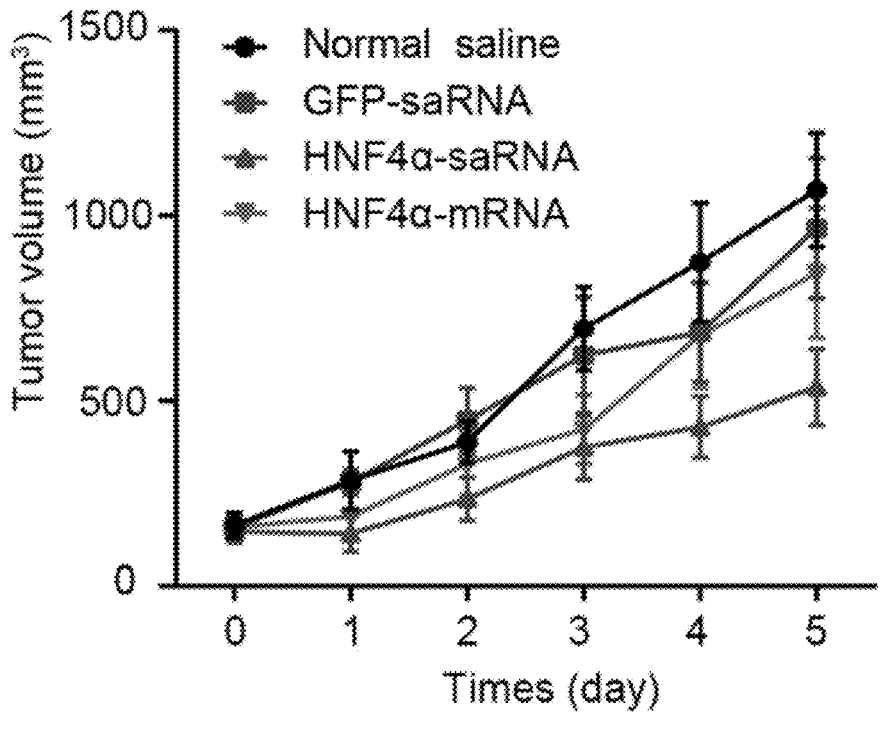
FIG. 14 shows tumor proliferation curves of subcutaneous Huh7 xenografts in test animals treated with HNF4 alpha-saRNA and HNF4 alpha-mRNA. GFP-saRNA is a self-replicating mRNA lipid nanoparticle control, and saline is a vehicle control.
Figure 15:
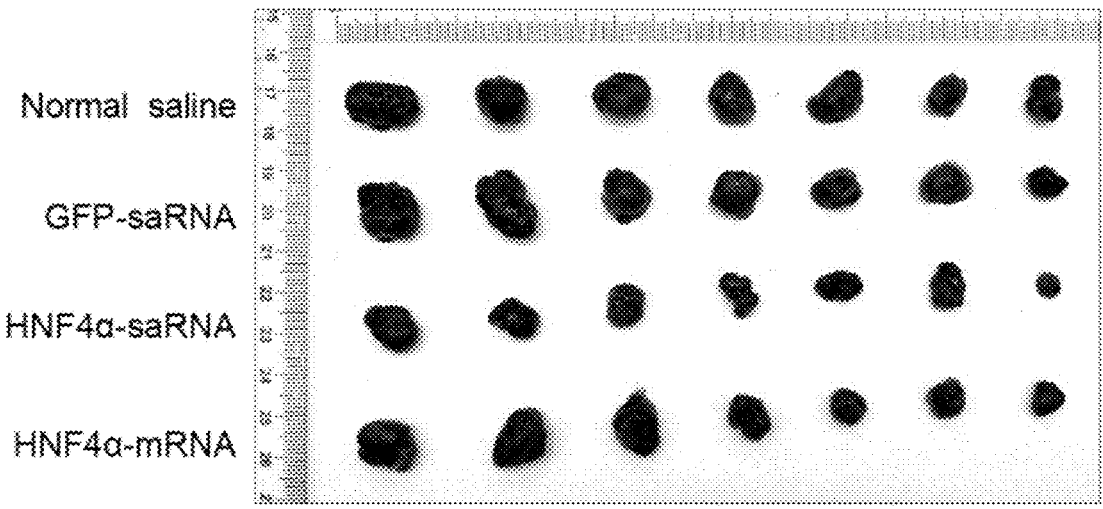
FIG. 15 shows a macroscopic picture of subcutaneous Huh7 tumors treated with HNF4 alpha-saRNA and HNF4 alpha-mRNA.
Figures 16A, 16B:
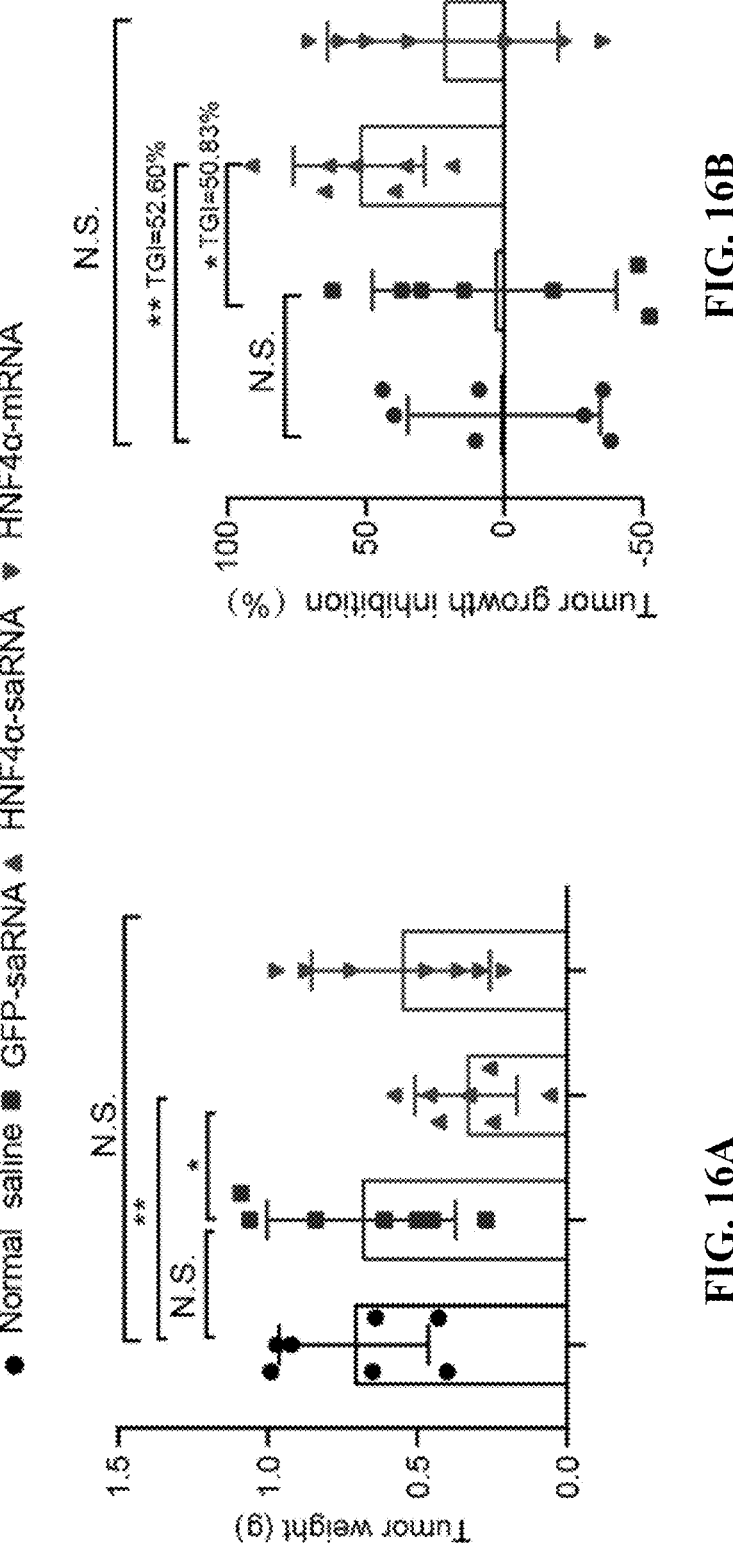
FIGS. 16A-B are graphs illustrating statistics of tumor weight (FIG. 16A) and tumor inhibition rate (FIG. 16B) in a subcutaneous xenograft model of Huh7 cells treated with HNF4 alpha-saRNA and HNF4 alpha-mRNA.
Figures 17, 18:
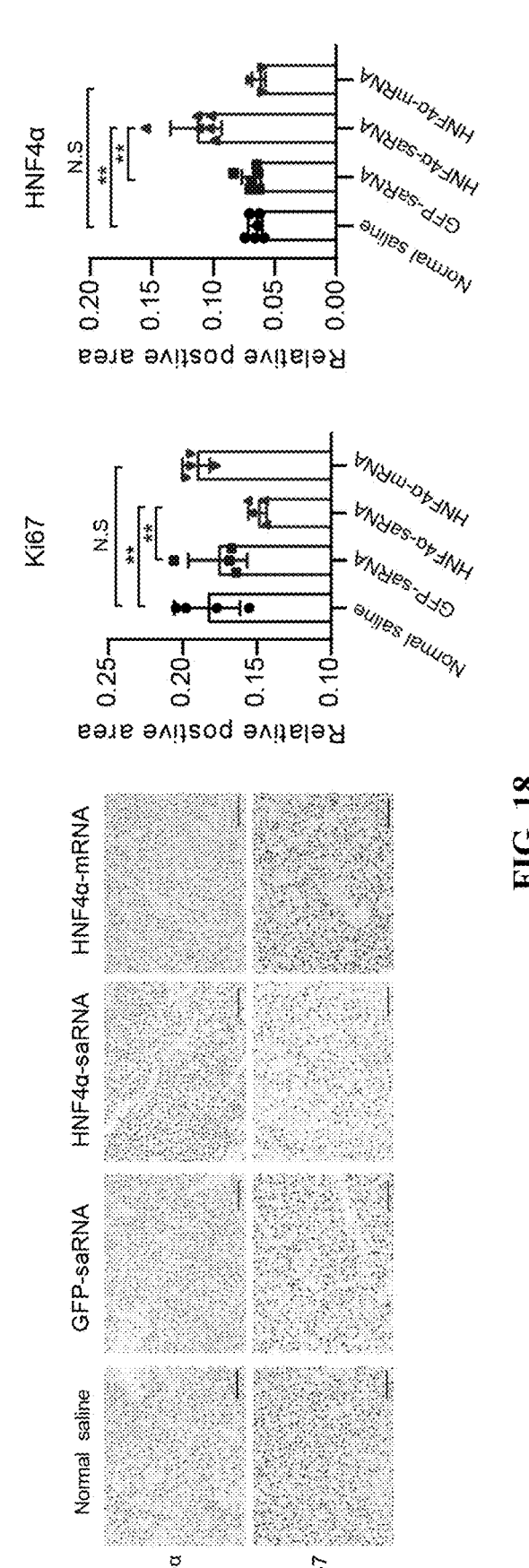
FIG. 17 shows the expression of HNF4 alpha in tumor tissues of a subcutaneous xenograft model of Huh7 cells treated with HNF4 alpha-saRNA by Western blot.
FIG. 18 shows expression changes of HNF4 alpha and Ki67 in tumor tissues by immunohistochemistry (left) and statistics of HNF4 alpha and Ki67 positive staining areas in tumor tissues (right).

3. HNF4 alpha-saRNA LNP inhibition of the growth of subcutaneous implant tumors in mice Five-week-old male nude mice (BALB/c immunodeficient strain) were purchased from Shanghai BK/KY Biotechnology, Inc., and housed under specific pathogen-free environmental conditions using a 12-hour alternative illumination cycle. $1 \times 10^6$ Huh-7 cells were injected subcutaneously into the right axilla of the male nude mice. Tumor sizes were measured in two dimensions using a vernier caliper, and the volume was calculated by the following formula: volume=length×(width)$^2$×½. When the average tumor volume reached approximately 100 mm$^3$, the mice were randomly divided into four groups (seven animals per group). Mice were intratumorally injected with 5 µg HNF4 alpha-saRNA LNP, GFP-saRNA LNP, HNF4 alpha-mRNA LNP or saline (vehicle control) with a final volume of 75 µl. Tumor volume was measured daily after injection, and tumor growth curves were plotted (FIG. 13 and FIG. 14). Five days after RNA injection, the mice were sacrificed, the tumors were excised and weighed (FIG. 15 and FIG. 16A), and the tumor inhibition rate was calculated (FIG. 16B). Some tumor tissues were embedded in paraffin wax and detected for HNF4 alpha expression by western-blot and immuno-histochemistry (FIG. 17 and FIG. 18), and the proliferative status of tumor cells was assessed by Ki67 staining (FIG. 18). The results show that intratumoral injection of HNF4 alpha-saRNA slows tumor growth, with more than 50% tumor inhibition (FIG. 16B), while HNF4 alpha-mRNA has a smaller tumor growth inhibition effect. The results of western-blot and immunohistochemistry show that HNF4 alpha-saRNA significantly increases the protein expression of HNF4 alpha in tumor tissues, and the expression of Ki67, a proliferation index of tumor cells, significantly decreases. These findings suggest that HNF4 alpha-saRNA effectively induces the expression of HNF4 alpha in cancer cells, and inhibits the growth of hepatocellular tumors in mice.

Figure 19:
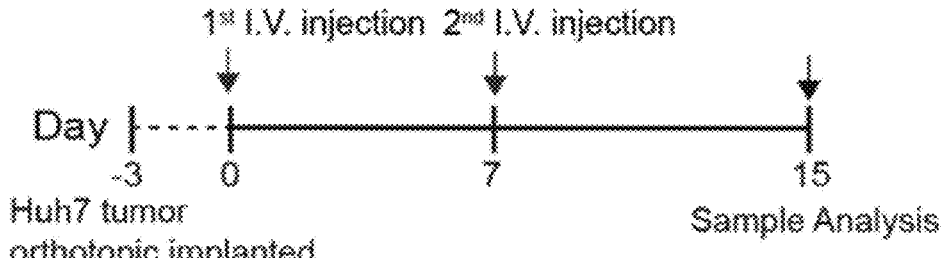
FIG. 19 shows an experimental flow diagram illustrating injection of self-replicating HNF4 alpha-saRNA and HNF4 alpha-mRNA lipid nanoparticles into the tail vein of test animals to treat a liver orthotopic implant of Huh7 cells in the test animals.
Figure 20:
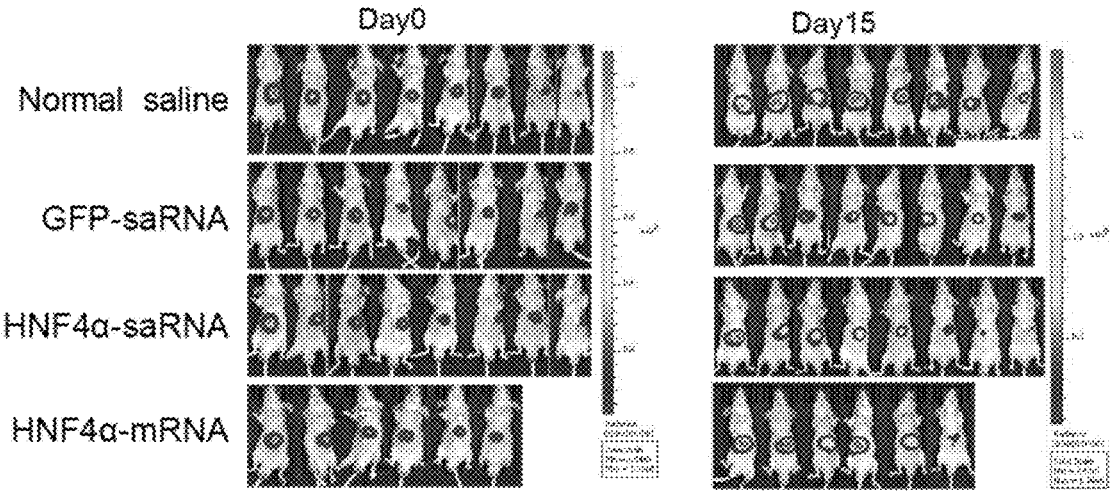
FIG. 20 is a graph illustrating in vivo fluorescence signals of mice before and after HNF4 alpha-saRNA and HNF4 alpha-mRNA injection in a liver orthotopic implant model of Huh7 cells. GFP-saRNA is a self-replicating RNA lipid nanoparticle control, and saline is a vehicle control.
Figure 21:
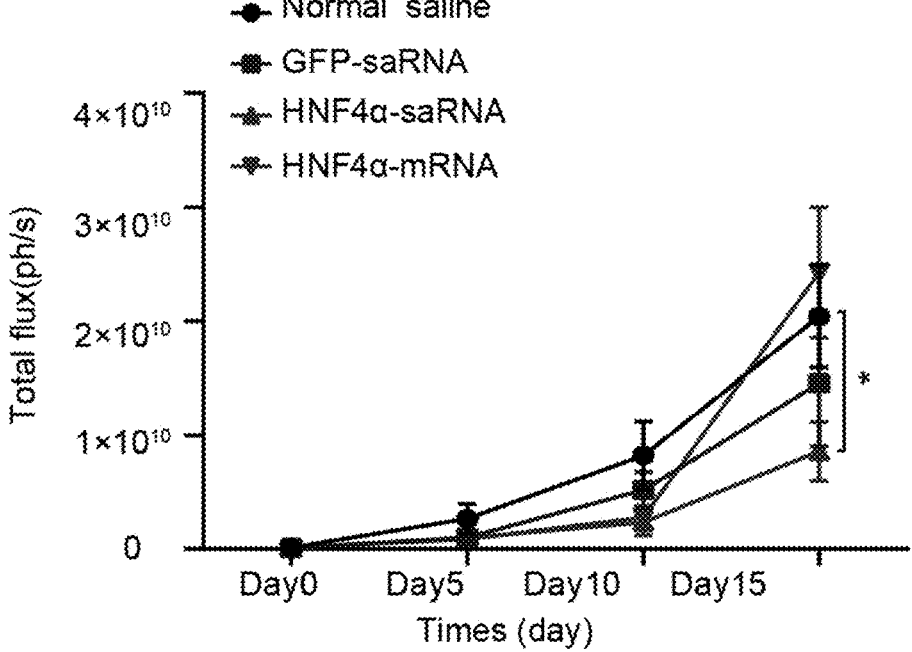
FIG. 21 is a graph illustrating statistics of in vitro fluorescence signals of mice at different time points during treatment of a liver orthotopic implant of Huh7 cells with HNF4 alpha-saRNA or HNF4 alpha-mRNA.
Figure 22:
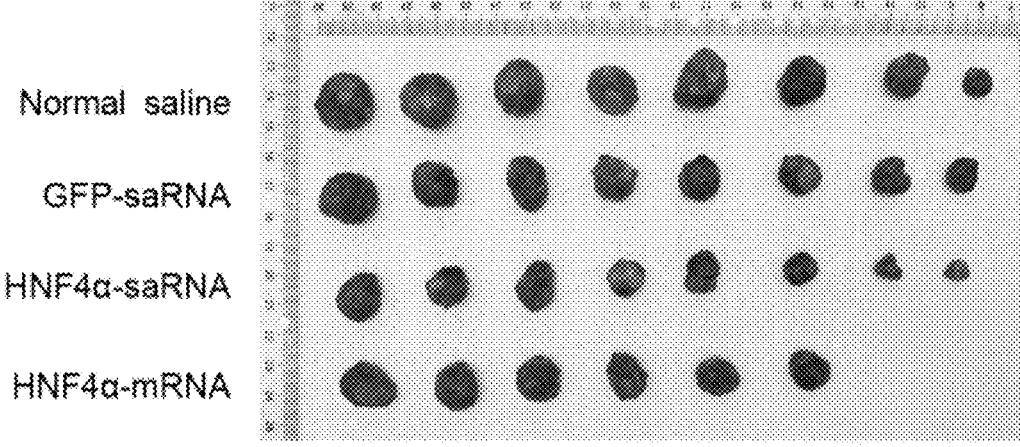
FIG. 22 is a macroscopic picture illustrating tumors in an experiment in which liver orthotopic implants of Huh7 cells into test animals were treated with HNF4 alpha-saRNA or HNF4 alpha-mRNA lipid nanoparticles.
Figure 23:
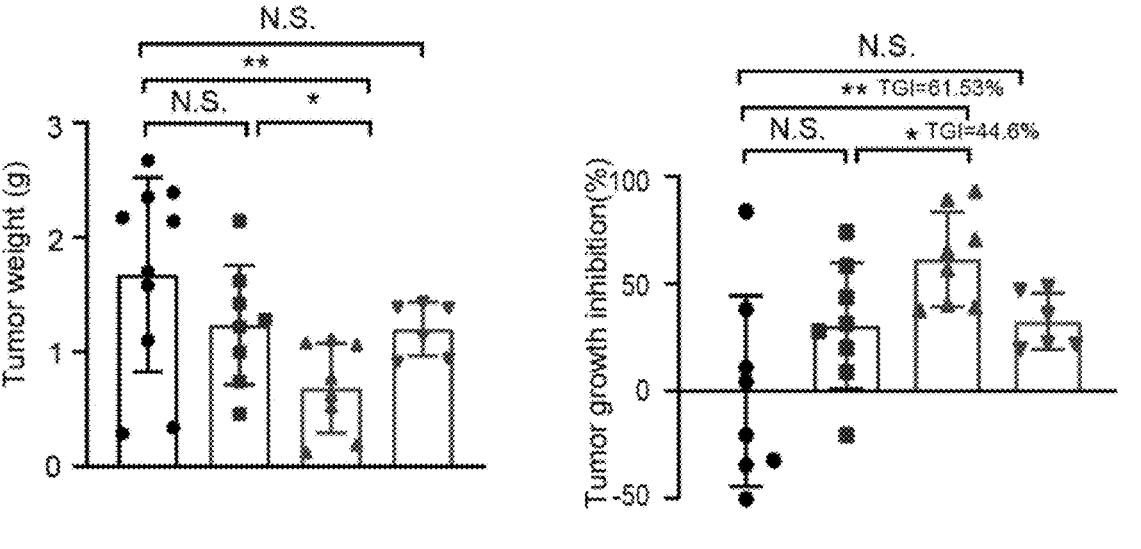
FIG. 23 shows the statistics of tumor weight (left) and tumor inhibition rate (right) in an experiment in which liver orthotopic implants of Huh7 cells into test animals were treated with HNF4 alpha-saRNA or HNF4 alpha-mRNA lipid nanoparticles.
Figure 24:
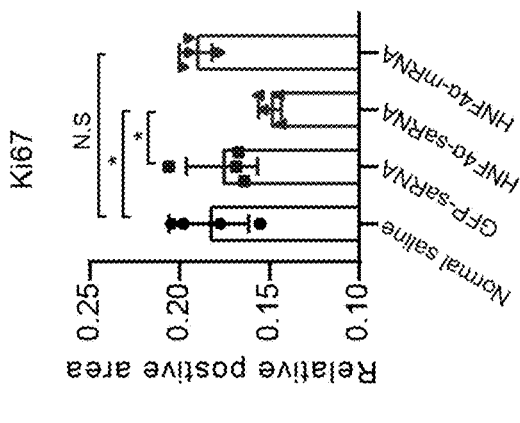
FIG. 24 shows the morphology of tumor tissues detected by HE staining, changes in Ki67 expression detected by immunohistochemistry (left), and statistics of a Ki67 positive staining area in tumor tissues (right).
Figure 24:
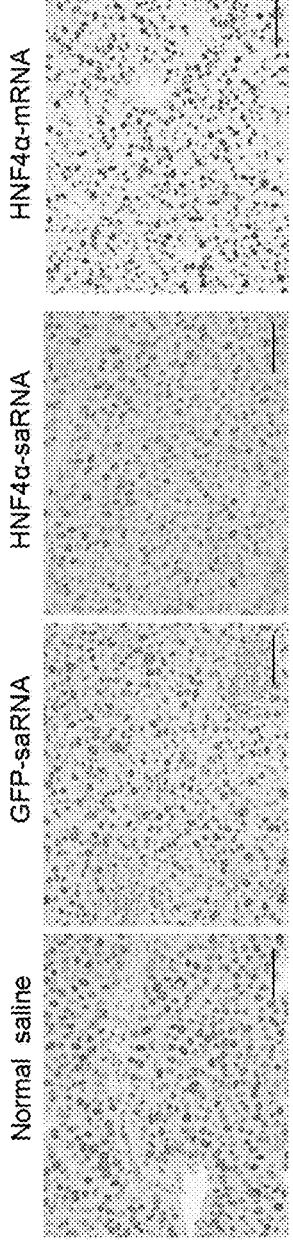
Figure 25:
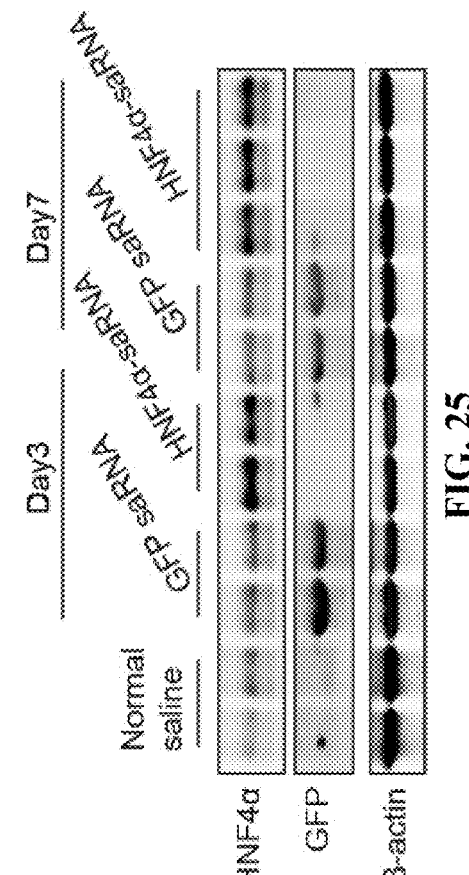
FIG. 25 shows the expression levels of HNF4 alpha protein detected by western blot of tumor tissues collected at different time points during treatment of liver orthotopic implants of Huh7 cells in test animals with HNF4 alpha-saRNA.
Figure 26:
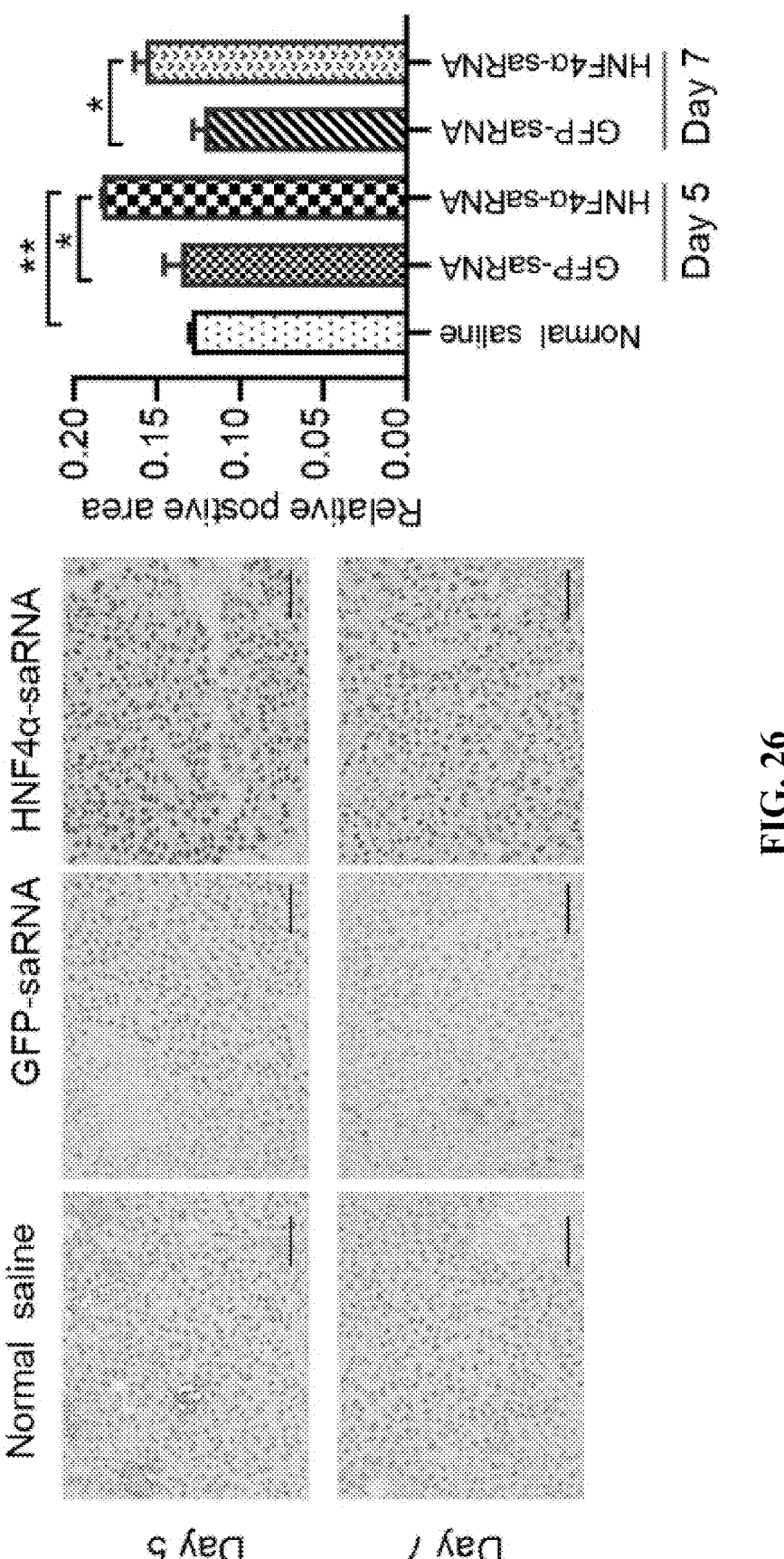
FIG. 26 shows changes in HNF4 alpha expression detected by immunohistochemistry (left) and statistics of an HNF4 alpha positive staining area in tumor tissues (right), collected at different time points during the treatment of liver orthotopic implants of Huh7 cells in test animals with HNF4 alpha-saRNA.
Figure 27:
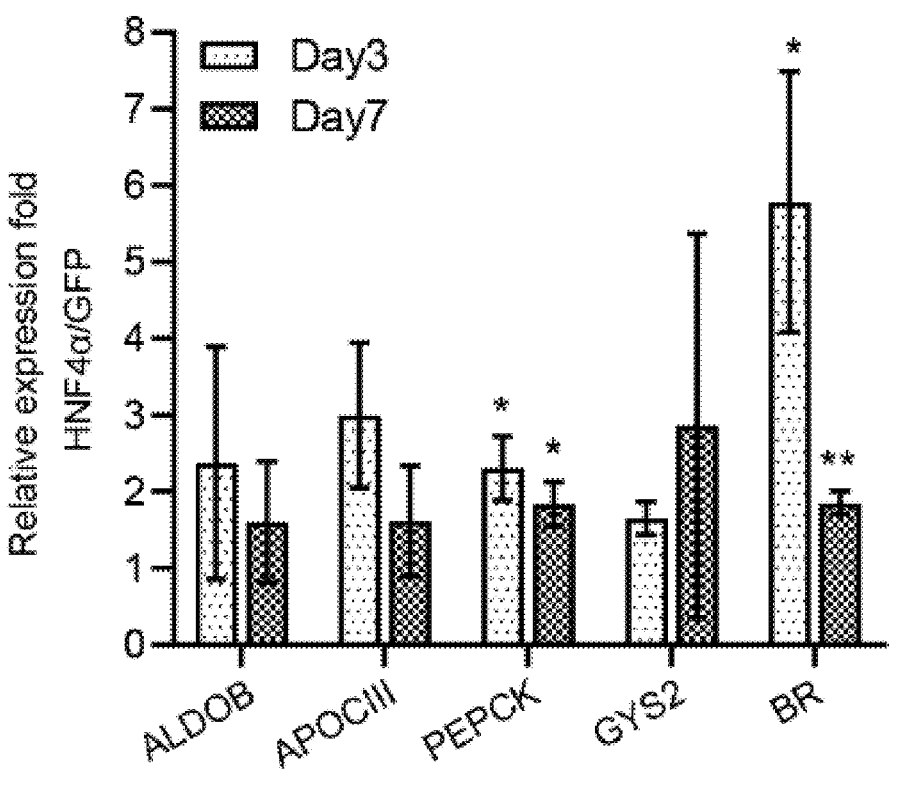
FIG. 27 shows expression of liver function-related genes detected by quantitative PCR in tumor tissues collected at different time points during the treatment of liver orthotopic implants of Huh7 cells in test animals with HNF4 alpha-saRNA.

4. HNF4 alpha-saRNA LNP inhibition of the growth of liver orthotopic implants in hepatoma cells The human hepatoma cell line Huh7, which stably expresses a luciferase gene, was seeded into the armpits of male nude mice. After tumor formation, the tumor mass was removed and cut into 1 mm$^3$ small pieces, and transplanted under the liver capsule of male nude bab/c mice. Tumor growth in the mice was monitored by an IVIS spectrum optical imaging system. After transplantation for 3 days, the mice were evenly divided into 4 groups (FIG. 20) according to the fluorescence signal value, and HNF4 alpha-saRNA LNP, GFP-saRNA LNP, HNF4 alpha-mRNA LNP, and saline (vehicle control) were administered via the tail vein at a dose of 2 mg/kg body weight (FIG. 19). The agent (HNF4 alpha-saRNA LNP, GFP-saRNA LNP, HNF4 alpha-mRNA LNP, or saline) was administered a second time to the mice via the tail vein 7 days after the initial administration. The efficacy of HNF4 alpha-saRNA was assessed by monitoring the growth of the mouse tumors based on bioluminescence (FIG. 20), and tumor growth curves were plotted (FIG. 21). At the end of the experiment, the mice were sacrificed, the tumors were excised, measured and weighed (FIG. 22), and tumor inhibition was calculated (FIG. 23). Tumor tissues were embedded in paraffin wax, HE staining was performed to assess tumor histomorphology and Ki67 staining was performed to assess the proliferative status of tumors (FIG. 24). The results show that the tumor growth is reduced after tail vein injection of HNF4 alpha-saRNA LNP, and the tumor inhibition rate is more than 40% compared with the control tumors/agents, while HNF4 alpha-mRNA LNP has a smaller tumor inhibition effect. At the same time, western blotting and immunohistochemistry were performed to detect the expression of HNF4 alpha in tumor tissues collected at different time points after LNP injection (FIG. 25 and FIG. 26), Ki67 staining was performed to assess the proliferative status of the tumors (FIG. 26), and quantitative PCR was performed to detect hepatocyte differentiation-related indicators (FIG. 27). The results show that HNF4 alpha-saRNA significantly up-regulates the expression of HNF4 alpha and the expression of liver function-related genes in tumor tissues. These results further suggest that HNF4 alpha-saRNA induces differentiation of hepatoma cells into normal hepatocytes, thereby inhibiting the growth of liver cancer.

Example 5: HNF4 Alpha-saRNA Inhibition of the Proliferation of Cholangiocarcinoma Cells 1. Up-regulation of HNF4 alpha expression in cholangiocarcinoma cells HuCC-T1 by HNF4 alpha-saRNA LNP at different concentrations Cholangiocarcinoma cells HuCC-T1 were seeded into a 6-well plate at a density of 40%-50% and cultured overnight.

Figure 28:
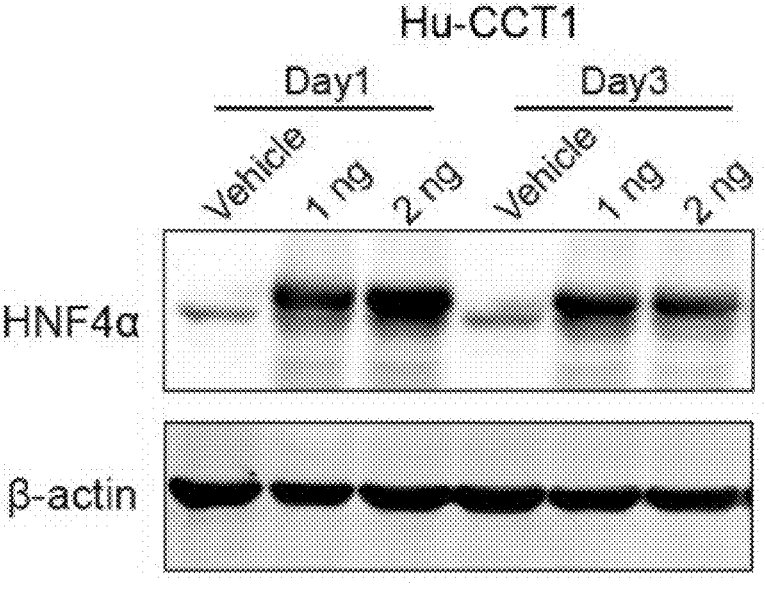
FIG. 28 shows an expression level of HNF4 alpha protein detected by western blot after cholangiocarcinoma cells HuCC-T1 were treated with different concentrations of HNF4 alpha-saRNA and HNF4 alpha-mRNA lipid nanoparticles for 1 and 3 days.

After washing with 1 ml of PBS, HNF4 alpha-saRNA LNP was added separately with serial dilutions in Opti-MEM (to a final concentration of 1 or 2 ng RNA/200 cells). After incubation for 6 hours, 1 mL of DMEM medium containing 20% FBS was added. Transfected cells were collected with RIPA lysate after 1 and 3 days for the detection of intracellular protein levels of HNF4 alpha by Western blot (FIG. 28). The results show that HNF4 alpha-saRNA LNP up-regulates the expression of HNF4 alpha in cholangiocarcinoma cells.

2. HNF4 alpha-saRNA LNP inhibition of the growth of cholangiocarcinoma cells

Figure 29:
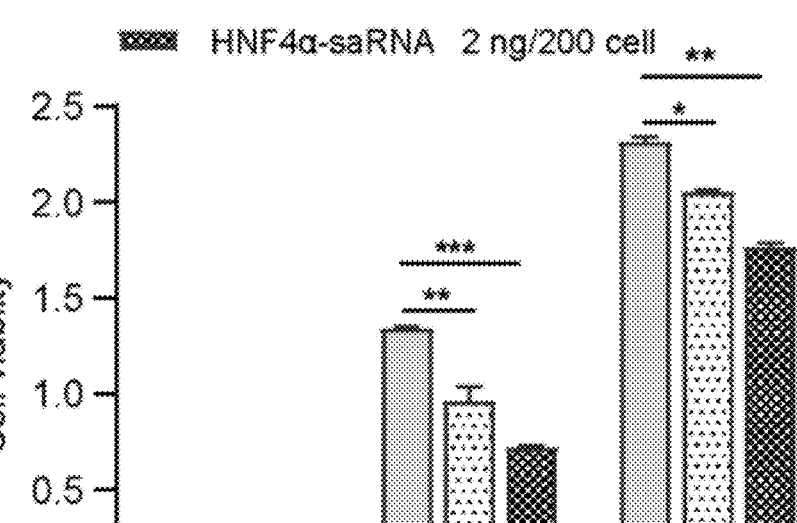
FIG. 29 is a graph that shows inhibition of the proliferation of cholangiocarcinoma cells HuCC-T1 by HNF4 alpha-saRNA LNP.

Cholangiocarcinoma cells HuCC-T1 were seeded into a 96-well plate at a density of $3 \times 10^3$ cells/well. After overnight culture, the medium supernatant was pipetted and the cells were washed with 100 µl of PBS. Different concentrations of HNF4 alpha-saRNA LNP diluted in Opti-MEM (to a final concentration of 1 or 2 ng RNA/200 cells) were added to the cells. After 6 hours, an equal volume of 20% FBS was added to the culture fluid of the corresponding cells to produce a 10% FBS concentration in the culture fluid. Cell proliferation was measured daily using a cell counting kit-8 (CCK-8, from Dojindo) to clarify the effect of RNA on tumor cell proliferation ability. The results show that HNF4 alpha-saRNA LNP significantly inhibits the proliferation of cholangiocarcinoma cells compared with control cells (FIG. 29).

3. HNF4 alpha-saRNA LNP inhibition of clonality of cholangiocarcinoma cells

Figure 30:
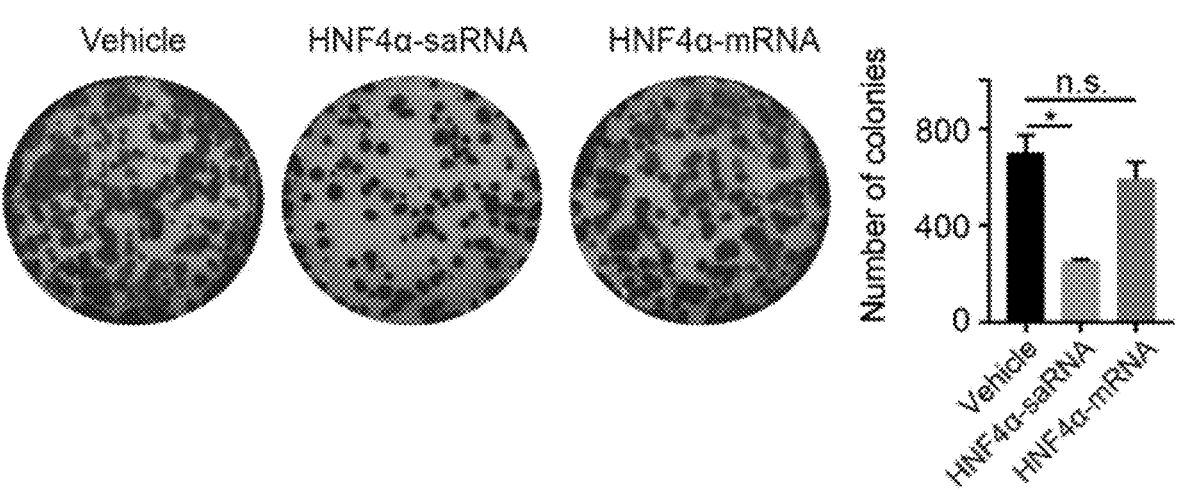
FIG. 30 shows effects of HNF4 alpha-mRNA LNP and HNF4 alpha-saRNA LNP on the clonality of cholangiocarcinoma cells HuCC-T1.

Cholangiocarcinoma cells HuCC-T1 were seeded into a 96-well plate at a density of $3 \times 10^3$ cells/well, cultured overnight, and transfected with HNF4 alpha-saRNA LNP and HNF4 alpha-mRNA LNP (2 ng/200 cell). After 24 hours, the trypsinized cells were transferred to a 60 mm culture dish and cultured. The culture fluid was changed every 3 days, and the clonality of tumor cells was observed microscopically. After cloning, the cloned tumor cells were washed with PBS twice, stained with crystal violet for 20 minutes, washed with PBS, dried and photographed, and the number of clones was counted by image J to clarify the effect of RNA on the clonality of tumor cells (FIG. 30). The results show that HNF4 alpha-saRNA significantly inhibits the clonality of cholangiocarcinoma cells, while HNF4 alpha-mRNA has a much smaller effect on the clonality of tumor cells.

Figure 31:
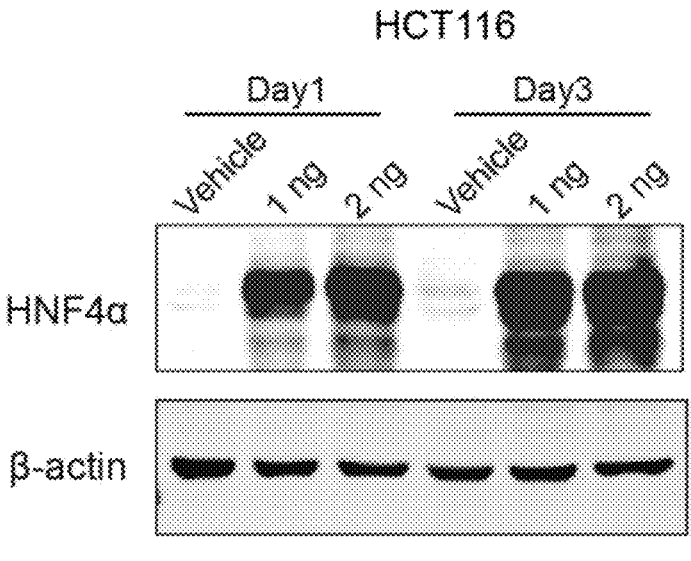
FIG. 31 shows the expression levels of HNF4 alpha protein detected by western blot after colon cancer cells HCT116 were treated with different concentrations of HNF4 alpha-saRNA LNP for 1 and 3 days.

Example 6: HNF4 Alpha-saRNA Inhibition of the Proliferation of Intestinal Cancer Cells 1. Up-regulation of HNF4 alpha expression in intestinal cancer cells HCT-116 by HNF4 alpha-saRNA LNP at different concentrations Intestinal cancer cells HCT-116 were seeded at 40%-50% density into a 6-well plate and cultured overnight. After washing with 1 ml of PBS, HNF4 alpha-saRNA LNP diluted in Opti-MEM (to a final concentration of 1 or 2 ng RNA/200 cells) was added. After incubation for 6 hours, 1 mL of DMEM medium containing 20% FBS was added. Transfected cells were collected with RIPA lysate after 1 and 3 days for the detection of intracellular protein levels of HNF4 alpha by Western blot (FIG. 31). The results show that HNF4 alpha-saRNA LNP up-regulates the expression of HNF4 alpha in intestinal cancer cells.

2. HNF4 alpha-saRNA LNP inhibition of the growth of cholangiocarcinoma cells

Figure 32:
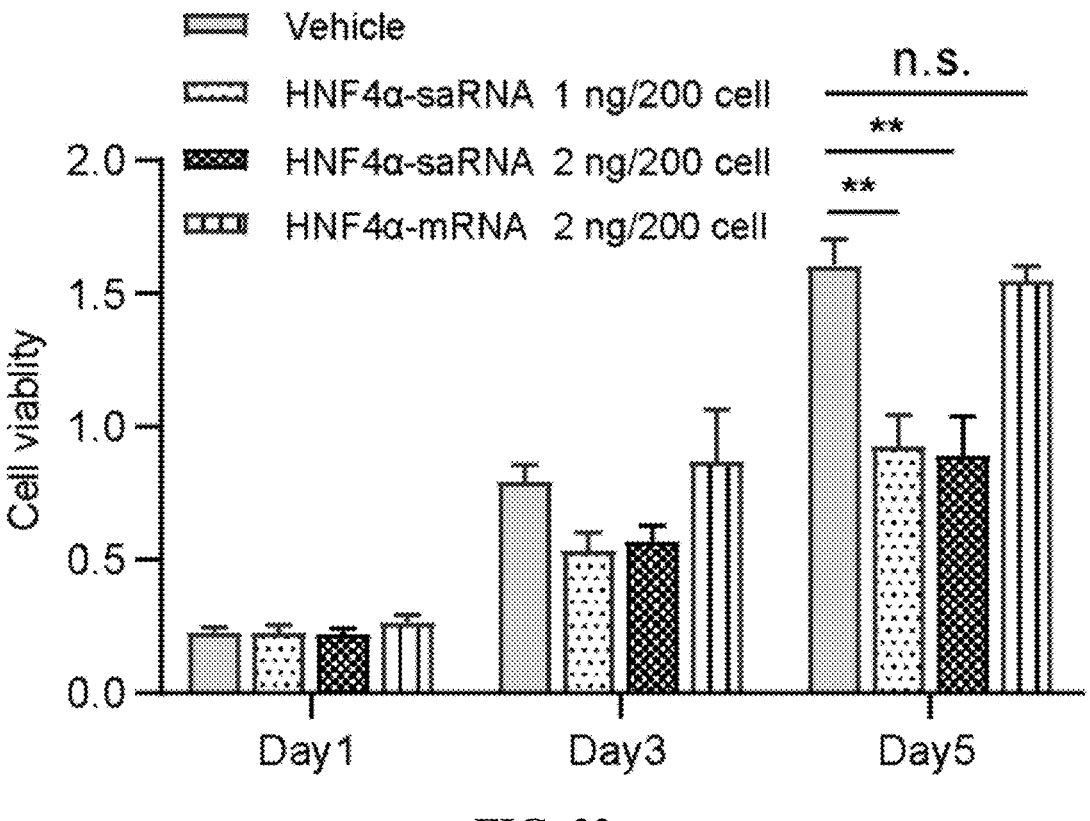
FIG. 32 is a graph that shows effects of HNF4 alpha-mRNA LNP and HNF4 alpha-saRNA LNP on proliferation of colon cancer cells HCT 116.
Figure 33:
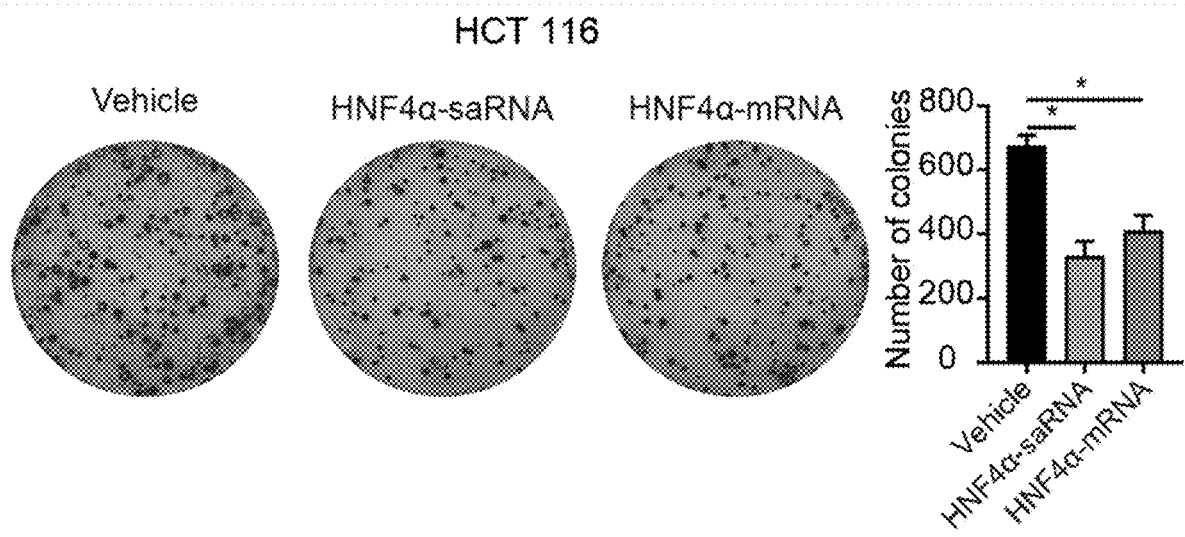
FIG. 33 shows effects of HNF4 alpha-mRNA LNP and HNF4 alpha-saRNA LNP on clonality of colon cancer cells HCT 116.

Intestinal cancer cells HCT-116 were seeded into 96-well plates at a density of $3 \times 10^3$ cells/well. After overnight culture, the medium supernatant was pipetted and the cells were washed with 100 µl of PBS. Different concentrations of HNF4 alpha-saRNA LNP and HNF4 alpha-mRNA LNP diluted in Opti-MEM (to a final concentration of 2 ng RNA/200 cells) were added to the cells. After 6 hours, an equal volume of 20% FBS was added to the culture fluid of the corresponding cells to produce a 10% FBS concentration in the culture fluid. Cell proliferation was measured daily using a cell counting kit-8 (CCK-8, Dojindo) to clarify the effect of RNA on tumor cell proliferation ability. The results show that HNF4 alpha-saRNA LNP significantly inhibits the proliferation of intestinal cancer cells compared with control cells (FIG. 32), while HNF4 alpha-mRNA LNP has no significant effect on tumor cell proliferation. 3. HNF4 alpha-saRNA LNP inhibition of clonality of intestinal cancer cells Intestinal cancer cells HCT-116 were seeded into a 96-well plate at a density of $3 \times 10^3$ cells/well, cultured overnight, and transfected with HNF4 alpha-saRNA LNP and HNF4 alpha-mRNA LNP (2 ng/200 cell). After 24 hours, the trypsinized cells were transferred to a 60 mm culture dish and cultured. The culture fluid was changed every 3 days, and the clonality of tumor cells was observed microscopically. After cloning, the cloned tumor cells were washed with PBS twice, stained with crystal violet for 20 min, washed with PBS, dried and photographed. The number of clones was counted by image J to clarify the effect of RNA on the clonality of the tumor cells (FIG. 33). The results show that HNF4 alpha-saRNA significantly inhibits the clonality of intestinal cancer cells, while HNF4 alpha-mRNA has a smaller effect on the clonality of tumor cells.

Figure 34:
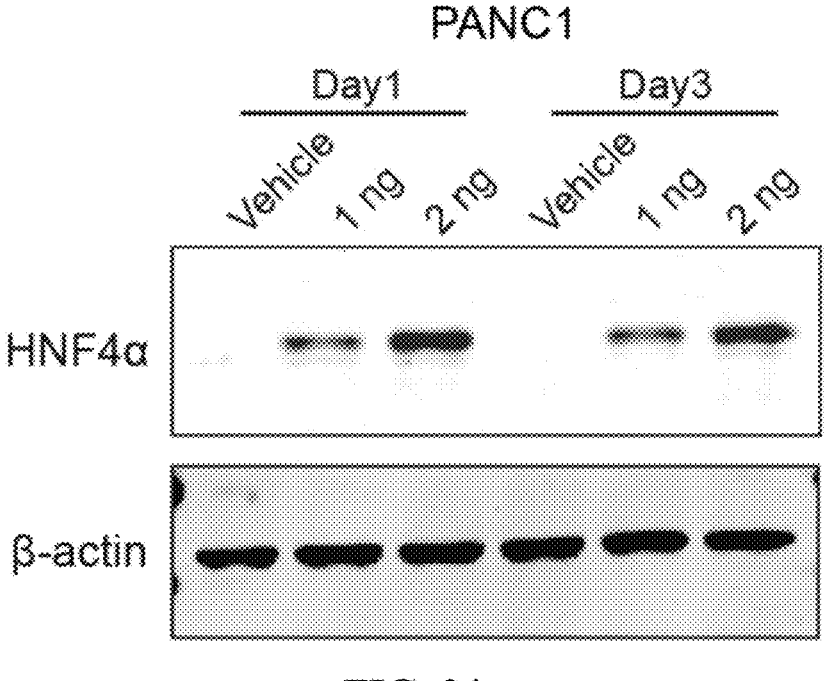
FIG. 34 shows the expression levels of HNF4 alpha protein detected by western blot after pancreatic cancer cells PANC1 were treated with different concentrations of HNF4 alpha-saRNA lipid nanoparticles for 1 and 3 days.

Example 7: HNF4 Alpha-saRNA Up-Regulation of the Expression of HNF4 Alpha in Pancreatic Cancer Cells Human pancreatic cancer cells PANC1 were seeded into a 6-well plate at a density of 40%-50% and cultured overnight. After washing with 1 ml of PBS, HNF4 alpha-saRNA LNP was added separately with serial dilutions in Opti-MEM (to a final concentration of 1 or 2 ng RNA/200 cells). After incubation for 6 hours, 1 mL of DMEM medium containing 20% FBS was added. Transfected cells were collected with RIPA lysate after 1 and 3 days for the detection of intracellular protein levels of HNF4 alpha by Western blot (FIG. 34). The results show that HNF4 alpha-saRNA LNP up-regulates the expression of HNF4 alpha in pancreatic cancer cells.

Example 8: HNF4 Alpha-saRNA LNP Up-Regulation of HNF4 Alpha Expression in Tumor Tissue In Vivo The human hepatoma cell line Huh7, which stably expresses a luciferase gene, was seeded into the armpits of male nude mice. After tumor formation, the tumor mass was removed and cut into 1 $mm^3$ pieces, transplanted under the liver capsule of male Bab/c nude mice, and the tumor growth in the mice was monitored by an IVIS spectrum optical imaging system.

Figure 35A:
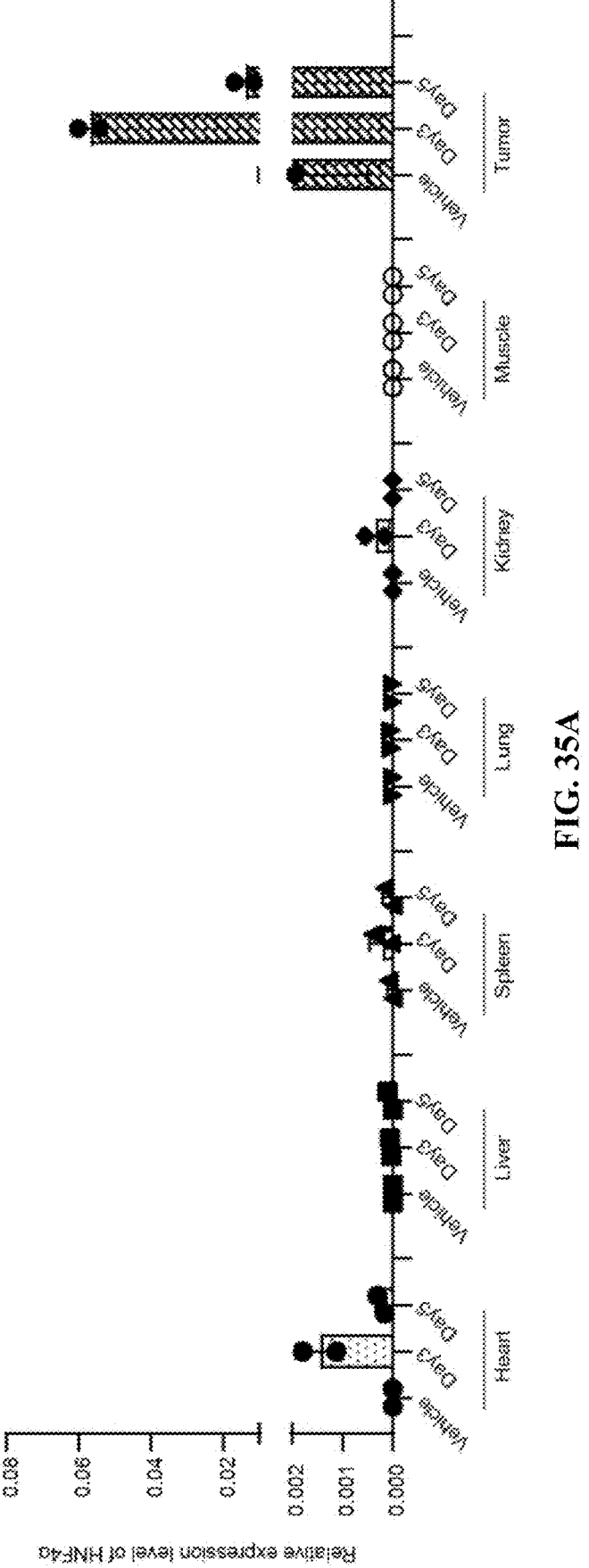
FIGS. 35A-B show levels of mRNA (HNF4 alpha) of HNF4 alpha and a conventional self-replicating RNA vector (VEEV) by quantitative PCR in tumor tissues and various normal tissues collected at different time points during the treatment of liver orthotopic implants of Huh7 cells in test animals with HNF4 alpha-saRNA.
Figure 35B:
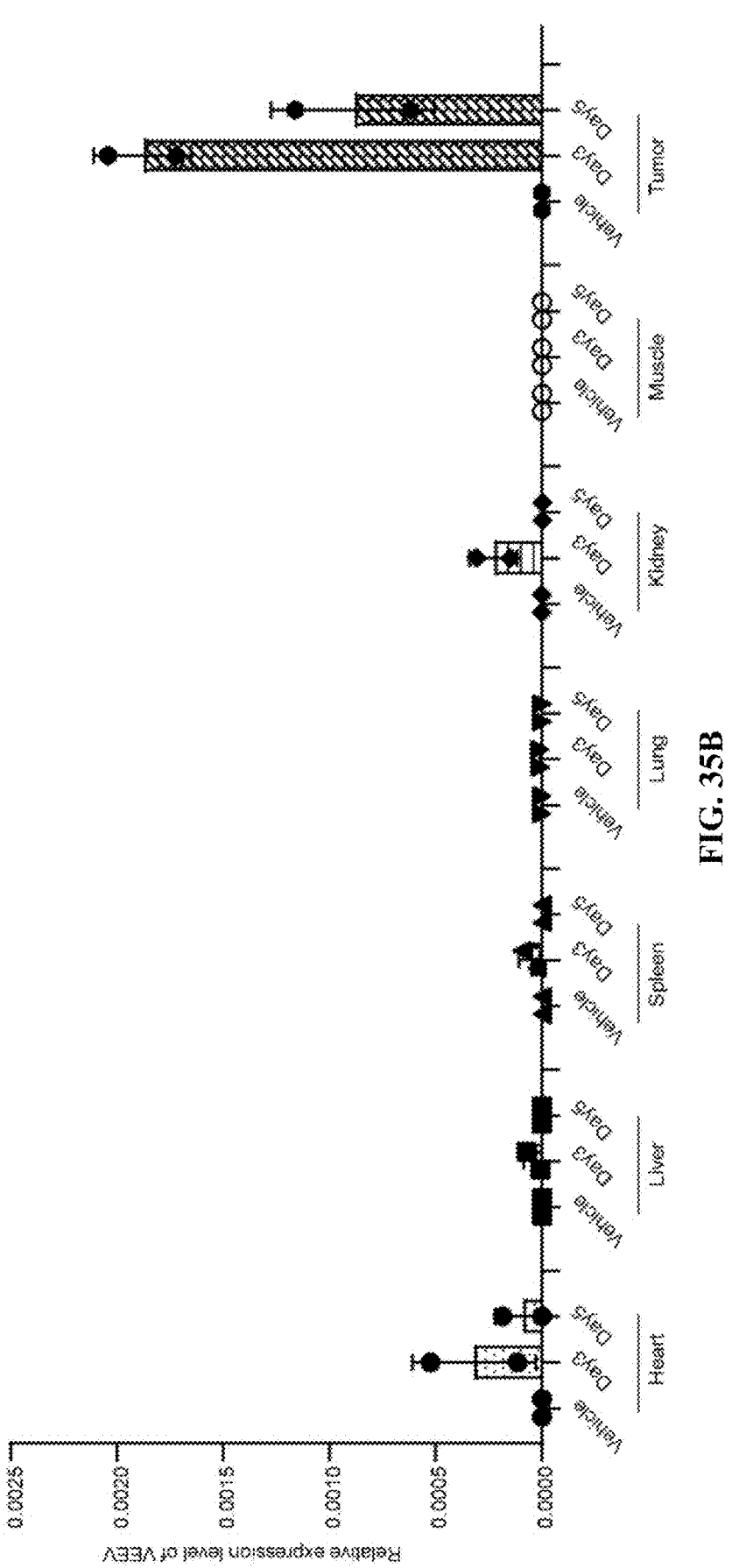
Figures 36A, 36B, 36C, 36D, 37A, 37B, 37C, 37D:
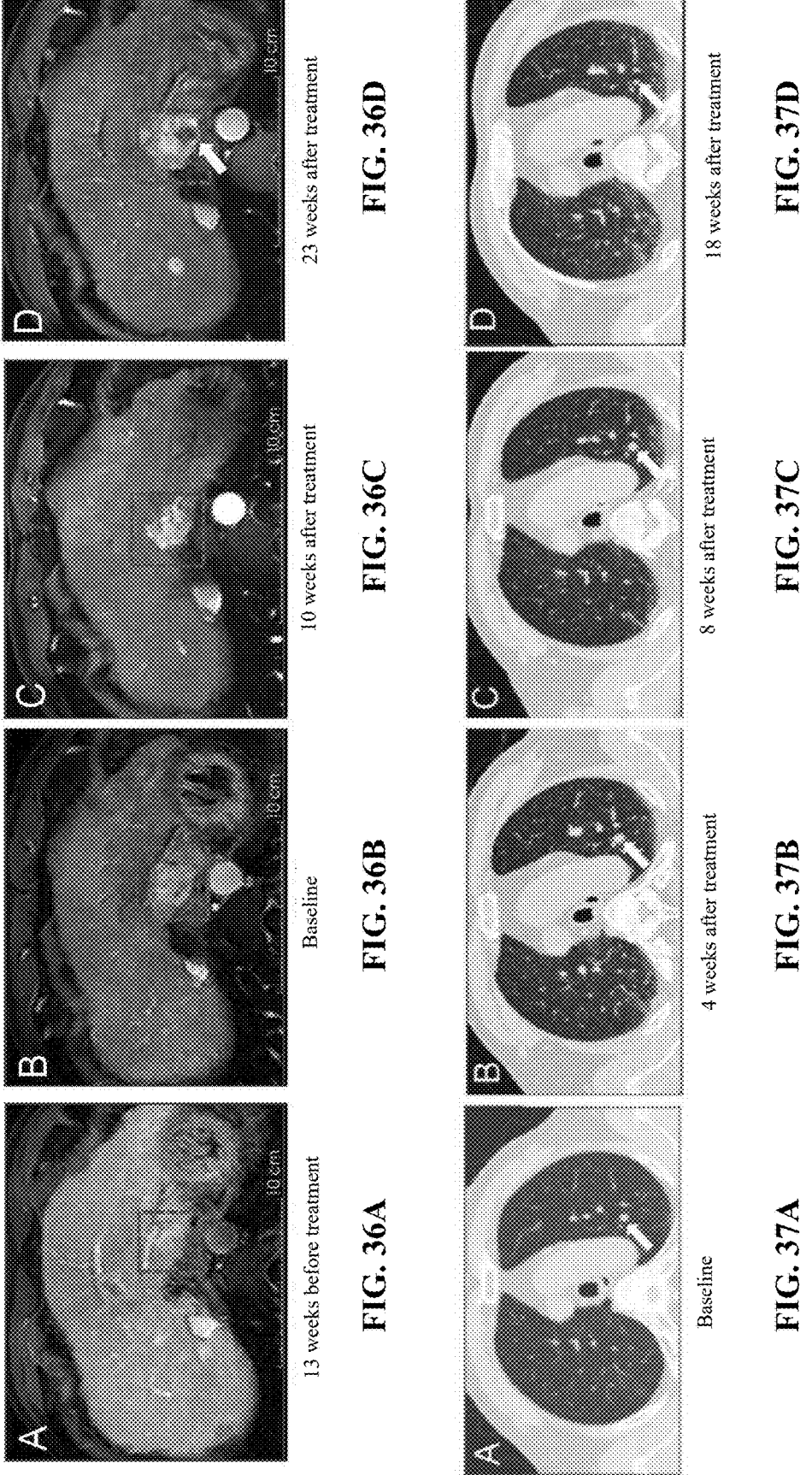
FIGS. 36A-D are enhanced MRIs showing liver cancer lesions remaining generally stable after treatment with HNF4 alpha-saRNA LNP.
FIGS. 37A-D are chest CT scans showing a lung metastatic lesion of a test animal with liver cancer gradually shrinking after treatment with HNF4 alpha-saRNA LNP.
Figures 38A, 38B, 38C, 38D:
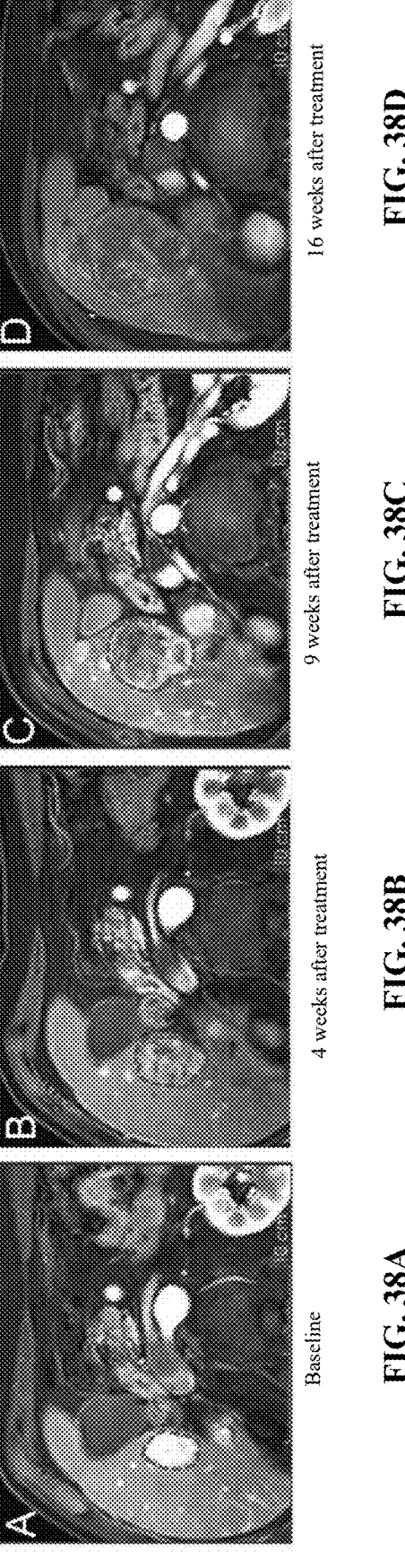
FIGS. 38A-D are enhanced MRIs showing changes in a liver cancer target lesion after treatment with HNF4 alpha-saRNA LNP.

When the tumors grew to a suitable size, HNF4 alpha-saRNA LNP was injected into the tail vein of each mouse at a dose of 2 mg/kg body weight, and tissues of each organ and the tumor(s) in the mice were taken 3 days and 5 days after injection, respectively. The expression distribution of alphavirus genome sequence (VEEV) and LNP-mediated human HNF4 alpha gene sequence in various organs and tumors was detected by quantitative PCR (FIGS. 35A-B). The results show that 3 days after tail vein injection, VEEV and human HNF4 alpha RNA is detected in the heart, spleen and kidney, but the VEEV and HNF4 alpha gene sequences are hardly detectable in the liver, lung and muscle tissues, and a high level of both VEEV and HNF4 alpha RNA is clearly detected in the tumor tissue. Five (5) days after tail vein injection, VEEV and human HNF4 alpha RNA are not detected in the organs except for an extremely trace amount of expression in the heart, but the VEEV and HNF4 alpha gene sequences could still be clearly detected in tumor tissues (FIGS. 35A-B). This suggests that self-replicating RNA mediates HNF4 alpha expression in tumor cells in vivo.

Example 9: HNF4 Alpha-saRNA LNP Treatment of Advanced Liver Cancer in Patients

GMP-compliant HNF4 alpha-saRNA LNP preparations were produced according to pharmaceutical standards by a reputable contract development and manufacturing organization (CDMO), and a single-dose toxicity test of the HNF4 alpha-saRNA LNP preparations was completed by a reputable contract research organization (CRO). The specific toxicity test process and results are as follows: Rats were administered the preparation once by tail vein injection, with an observation period of 14 days. A negative control group (0.9% sodium chloride injection), a vector control group (LNP solution only) and a test article group (the HNF4 alpha-saRNA preparation, 150 μg/body) were set up, and given the corresponding agent (0.9% NaCl, LNP only, or HNF4 alpha-saRNA LNP preparation). All animals survived to the scheduled dissection day. At the end of the observation period, no abnormality was observed in gross necropsy, and no histopathological changes related to the test article were observed.

Following the acute toxicity test, an investigator-initiated clinical trial was conducted using hepatic arterial cannula administration, and dose escalation trials of 25 μg, 50 μg, and 100 μg were completed (3 patients in each group). None of the 9 patients experienced dose-limiting toxicities or Grade 3 or above treatment-related adverse events and serious adverse events. Four patients had no obvious progression of liver cancer lesions after treatment for 5 months or more, including one patient with significant reduction in lung metastases (FIGS. 36A-D) and another patient with focal necrosis of liver cancer lesions (FIGS. 37A-D). Three patients had marked necrosis of target lesions with a marked reduction in enhancement (FIGS. 38A-D). The preliminary results show that the HNF4 alpha-saRNA LNP preparation has a favorable safety profile and significantly inhibits tumor growth in patients with advanced liver cancer.

Preferred implementations of the present invention are specifically described, but the present invention is not limited to the examples. Those skilled in the art can make equivalent variations or replacements without departing from the spirit of the present invention, and these equivalent variations or replacements are included in the scope defined by claims of the present application.

What is claimed is:

1. A gene delivery system, comprising a nucleic acid vector and a delivery vehicle, wherein the nucleic acid vector is a self-replicating RNA encoding HNF4 alpha; the gene delivery system delivers the HNF4 alpha or the self-replicating RNA into tumor cells, induces differentiation of the tumor cells into normal mature cells, inhibits proliferation of the tumor cells, and/or induces apoptosis of the tumor cells; the self-replicating RNA has a 35-100 nt polyadenine tail and is an engineered alphavirus genome that includes a 5'-cap, a non-coding or untranslated region (5' UTR), four genes encoding nonstructural proteins that enable RNA replication, a 26S subgenome promoter, a gene encoding the HNF4 alpha replacing structural protein sequences of the engineered alphavirus genome, and a 3' non-coding or untranslated region (3' UTR); and the delivery vehicle comprises lipid-based nanoparticles.

2. The gene delivery system according to claim 1, wherein the self-replicating RNA has or carries a 60-75 nt polyadenine tail.

3. The gene delivery system according to claim 1, wherein the self-replicating RNA has or carries a 67 nt polyadenine tail.

4. The gene delivery system according to claim 1, wherein the self-replicating RNA includes the sequence shown in SEQ ID NO:3.

5. The gene delivery system according to claim 1, wherein the lipid-based nanoparticles comprise:
   1,2-distearoyl-sn-glycero-3-phosphocholine or 1,2-dioleoyl-sn-glycero-3-phosphorylethanolamine, in an amount of ranging from 5% to 20% by moles;
   cholesterol, in an amount of ranging from 30% to 55% by moles;
   dimyristoylglycerol-polyethylene glycol 2000 or a lipid containing a polyethylene glycol chain, in an amount of ranging from 0.5% to 3% by moles; and
   one or more ionizable lipids, in an amount of ranging from 30% to 60% by moles.

6. The gene delivery system according to claim 5, wherein the lipid-based nanoparticles have a particle size of 40-300 nm.

7. A pharmaceutical composition, comprising the gene delivery system according to claim 1.

8. The gene delivery system according to claim 5, wherein the one or more ionizable lipids comprise an N-acyloxyalkyl N-hydroxyalkylamine.

9. The gene delivery system according to claim 5, wherein the N-acyloxyalkyl N-hydroxyalkylamine has a formula $NR^1R^2R^3$, where $R^1$ is an ω-hydroxy-$C_2$-$C_{10}$-alkyl or an ω-hydroxy-$C_4$-$C_{10}$-dialkylene ether group, and $R^2$ and $R^3$ are independently a $C_4$-$C_{10}$-alkylene group substituted with a straight-chain or branched $C_{10}$-$C_{20}$-alkanoyloxy group.

10. The gene delivery system according to claim 5, wherein the one or more ionizable lipids comprise N,N-bis [6-(2-hexyldecanoyl)oxyhexyl]-4-hydroxy-butylamine, 8-[(2-hydroxyethyl) [6-oxo-6-(undecyloxy) hexyl]amino]-octanoic acid, 1-octylnonyl ester, or (2-hydroxyethyl)ethyl-azanediylbis(hexane-6,1-diyl)bis(2-hexyldecanoate).

11. The gene delivery system according to claim 5, wherein the 1,2-distearoyl-sn-glycero-3-phosphocholine or 1,2-dioleoyl-sn-glycero-3-phosphorylethanolamine is distearoyl-sn-glycero-3-phosphocholine (DSPC), and the dimyristoylglycerol-polyethylene glycol 2000 or the lipid containing a polyethylene glycol chain is dimyristoylglycerol-polyethylene glycol 2000 (DMG-PEG 2000).

12. The gene delivery system according to claim 11, wherein the DSPC, the cholesterol, the DMG-PEG 2000 and the one or more ionizable lipids are present in a molar ratio of DSPC:cholesterol: DMG-PEG 2000: ionizable lipid(s) of 9.4:42.5:1.8:46.3.

13. The gene delivery system according to claim 1, wherein the lipid-based nanoparticles comprise 1,2-distearoyl-sn-glycero-3-phosphocholine or 1,2-dioleoyl-sn-glycero-3-phosphorylethanolamine, cholesterol, a lipid containing a polyethylene glycol chain, and one or more ionizable lipids.

* * * * *